(12) United States Patent
King

(10) Patent No.: US 6,287,559 B1
(45) Date of Patent: Sep. 11, 2001

(54) CLONING AND RECOMBINANT PRODUCTION OF VESPID VENOM HYALURONIDASES, AND IMMUNOLOGICAL THERAPIES BASED THEREON

(75) Inventor: Te Piao King, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 08/474,853

(22) Filed: Jun. 7, 1995

Related U.S. Application Data

(60) Division of application No. 08/180,209, filed on Jan. 11, 1994, now Pat. No. 5,593,877, which is a continuation-in-part of application No. 08/031,400, filed on Mar. 11, 1993, now abandoned.

(51) Int. Cl.⁷ .............................. A61K 38/51; C12N 9/26; C12N 1/20; C07H 21/04
(52) U.S. Cl. ..................... 424/94.62; 435/201; 435/69.1; 435/252.3; 435/320.1; 536/23.2; 536/23.5; 536/23.4; 530/350
(58) Field of Search .......................... 424/94.62; 435/201, 435/69.1, 320.1, 252.5; 530/350; 536/23.2, 23.5

(56) References Cited

U.S. PATENT DOCUMENTS

| | | | |
|---|---|---|---|
| 4,469,677 | 9/1984 | Michael et al. | 424/276.1 |
| 4,822,608 | 4/1989 | Benton et al. | 424/539 |
| 5,532,142 * | 7/1996 | Johnston et al. | 435/69.1 |

FOREIGN PATENT DOCUMENTS

WO 92/03551 3/1992 (WO).

OTHER PUBLICATIONS

Gmachl et al. (1993) Proc. Natl. Acad. Sci. USA 90:3569–73.
Gmachl et al. (1993) FEBS Lett. 336:545–8.
Lu et al. (1993) *J. Allergy Clin. Immunol.*, 93:224(#367).
Soldatova, 1993, *J. Allergy Clin. Immunol.*, 91:283(#568).
King et al., 1993, *J. Allergy Clin. Immunol.*, 91:283(#569).
Lu et al. (1993) J. Immunol. 150:2823–30.
Soldatova (1993) FEBS Letters 320:145–9.
Dhillon et al., *J. Allergy Clin. Immunol.*, 90:42–51 1992.
Dhillon et al. (1992) *J. Allergy Clin. Immunol.* 89:174 (#119).
Gaur et al., *Science*, 259:1491–1494 1992.
Griffith et al., *Gene.*, 113:263 1992.
Jacobsen et al. (1992) *J. Allergy Clin. Immunol.*, 89:292(#591).
Scheiner (1992) Int. Arch. Allerg. Immunol. 98:93–6.
Valenta et al., *J. Exp. Med.*, 175:377 1992.
Ales–Martinez et al., *Immunol. Today*, 12:201 1991.
Fehlner et al., *J. Immunol.*, 146:799 1991.
Gammon et al., *Immunol. Today*, 12:193 1991.
Griffith et al., *Int. Arch. Allergy Appl. Immunol.*, 96:296 1991.
Han et al., *J. Allergy Clin. Immunol.*, 87:327 (#752), 1991.
O'Hehir et al., *Ann. Rev. Immunol.*, 9:67 1991.
O'Hehir et al., *J. Allergy Clin. Immunol.*, 87:1120 1991.
Rafnar et al., *J. Biol. Chem.*, 266:1229 1991.
Rudensky et al. (1991) Nature 353:622–7.
Silvanovich et al., *J. Biol. Chem.*, 266:1204 1991.
Valenta et al., *Science*, 253:557 1991.
Aruda et al., *J. Exp. Med.*, 172:1529 1990.
King et al., *Protein Sequences and Data Analysis*, 3:263–6 1990.
King, *J. Allerg. clin. Immunol.*, 85:213 (#280), 1990.
Perez et al., *J. Biol. Chem.*, 265:16210 1990.
Ansari et al., *Biochemistry*, 28:8665 1989.
Breiteneder et al., *EMBO J.*, 8:1935 1989.
Hynes et al. (1989) Infect. Immunity 57:533–9.
Korneev et al. (1989) Bioorg. Khim. 15:127–7.
Chua et al., *J. Exp. Med.*, 167:175 1988.
Fang et al., *Proc. Natl. Sci. USA*, 85:895–9 1988.
Frohman et al., *Proc. Natl. Acad. Sci. USA*, 85:8998–9002 1988.
King, *J. Allergy Clin. Immunol.*, 79: 113 1987.
Reeck et al. (1987) Cell 50:667.
Hoffman *J. Allergy and Clin Immunol.*, 75:611 1985.
Huynh et al. (1985) pp. 49–78 in DNA Cloning, Glover, ed., IRL Press.
King et al., *J. Allergy and Clin. Immunol.* 75:621–8 1985.
Lathe et al. (1985) J. Mol. Biol. 183:1–12.
King et al., *Arch. Biochem. Biophys.*, 230:1 1984.
King et al., *J. Immunol.*, 133:2668 1984.
King et al., *Mol. Immunol.*, 20:297 1983.
King et al., *Biochemistry*, 17:5165 1978.

* cited by examiner

Primary Examiner—Tekchand Saidha
(74) Attorney, Agent, or Firm—Darby & Darby

(57) ABSTRACT

The present invention is directed to nucleic acids encoding vespid venom enzymes, or fragments thereof, recombinant vectors comprising such nucleic acids, and host cells containing the recombinant vectors. The invention is further directed to expression of such nucleic acids to produce recombinant vespid venom enzymes, or recombinant fragments, derivatives or analogs thereof. Such recombinant products are useful for diagnosis of allergy and for therapeutic treatment of allergy. In specific embodiments, the present invention provides nucleic acids encoding, and complete nucleotide and amino acids sequences for, vespid venom phospholipase, for example, *Dolichovespula maculata* phospholipase and *Vespula vulgaris* phospholipase, and vespid venom hyaluronidase, for example, *Dolichovespula maculata* hyaluronidase.

12 Claims, 13 Drawing Sheets

```
           R  L  I  M  F  V  G  D  P  S  S  S  N  E  L  D  R  F  S  V    3
         AGATTAATAATGTTCGTAGGTGATCCGTCGTCATCAAATGAATTAGATAGATTCTCCGTA   60

C  P  F  S  N  D  T  V  K  M  I  F  L  T  R  E  N  R  K  H   23
         TGTCCCTTTAGTAATGATACAGTTAAGATGATTTTTTTAACAAGGGAAAACCGAAAACAT   120

D  F  Y  T  L  D  T  M  N  R  H  N  E  F  K  K  S  I  I  K   43
         GATTTTTATACGCTAGATACAATGAACAGGCACAATGAATTTAAGAAGTCAATCATAAAA   180

R  P  V  V  F  I  T  H  G  F  I  S  S  A  T  E  K  N  F  V   63
         CGTCCAGTTGTATTCATTACGCATGGTTTTACTTCGTCTGCAACCGAAAAAAATTTCGTT   240

A  M  S  E  A  L  M  H  T  G  D  F  L  I  I  M  V  D  W  R   83
         GCTATGTCAGAGGCTCTTATGCATACAGGTGATTTTCTTATAATTATGGTCGATTGGCGG   300

M  A  A  C  T  D  E  Y  P  G  L  K  Y  M  F  Y  K  A  A  V  103
         ATGGCTGCTTGTACTGATGAATACCCAGGTCTGAAGTATATGTTTTATAAGGCTGCCGTT   360

G  N  T  R  L  V  G  N  F  I  A  M  I  A  K  K  L  V  E  Q  123
         GGTAATACACGCTTAGTTGGAAATTTTATCGCTATGATCGCAAAGAAACTTGTAGAACAA   420

Y  K  V  P  M  T  N  I  R  L  V  G  H  S  L  G  A  H  I  S  143
         TATAAAGTGCCGATGACAAATATACGACTGGTGGGACACAGTTTGGGCGCACACATTTCA   480

G  F  A  G  K  R  V  Q  E  L  K  L  G  K  F  S  E  I  I  G  163
         GGTTTCGCAGGCAAAAGAGTTCAAGAGTTAAAATTAGGAAAATTTTCTGAAATTATTGGG   540

L  D  P  A  G  P  S  F  K  K  N  D  C  S  E  R  I  C  E  I  183
         CTTGATCCTGCTGGGCCTAGTTTCAAGAAAAATGATTGTTCCGAGAGAATCTGCGAGACA   600

D  A  H  Y  V  Q  I  L  H  T  S  S  N  L  G  T  E  R  T  L  203
         GACGCACATTATGTACAAATTTTACATACATCGAGCAATTTAGGAACAGAGAGAACTCTT   660

G  T  V  D  F  Y  I  N  N  G  S  N  Q  P  G  C  R  Y  I  I  223
         GGCACCGTCGATTTCTACATAAATAACGGAAGTAATCAACCCGGTTGCAGATATATTATT   720

G  E  T  C  S  H  T  R  A  V  K  Y  F  T  E  C  I  R  R  E  243
         GGAGAAACTTGCTCTCATACGAGAGCCGTGAAATACTTTACCGAGTGCATAAGACGCGAA   780

C  C  L  I  G  V  P  Q  S  K  N  P  Q  P  V  S  K  C  T  R  263
         TGTTGTTTAATTGGGGTCCCGCAGTCCAAGAATCCGCAGCCTGTTTCGAAGTGCACAAGA   840

N  E  C  V  C  V  G  L  N  A  K  K  Y  P  K  R  G  S  F  Y  283
         AACGAGTGCGTTTGCGTTGGATTAAACGCAAAGAAATATCCTAAAAGGGGCTCATTTTAT   900

V  P  V  E  A  E  A  P  Y  C  N  N  N  G  K  I  I  *        300
         GTACCGGTTGAAGCTGAAGCTCCATATTGCAATAACAACGGGAAAATAATTTAATTATAT   960

AAAAAAAACATTACTATTGACACAAGTGCATTTGTTAATGATGAAATGAATAAATTACGA  1020

TTCAAGAAAAAAAAAAAAAAAAAAAAAAAAAA                              1050
```

FIG. 1

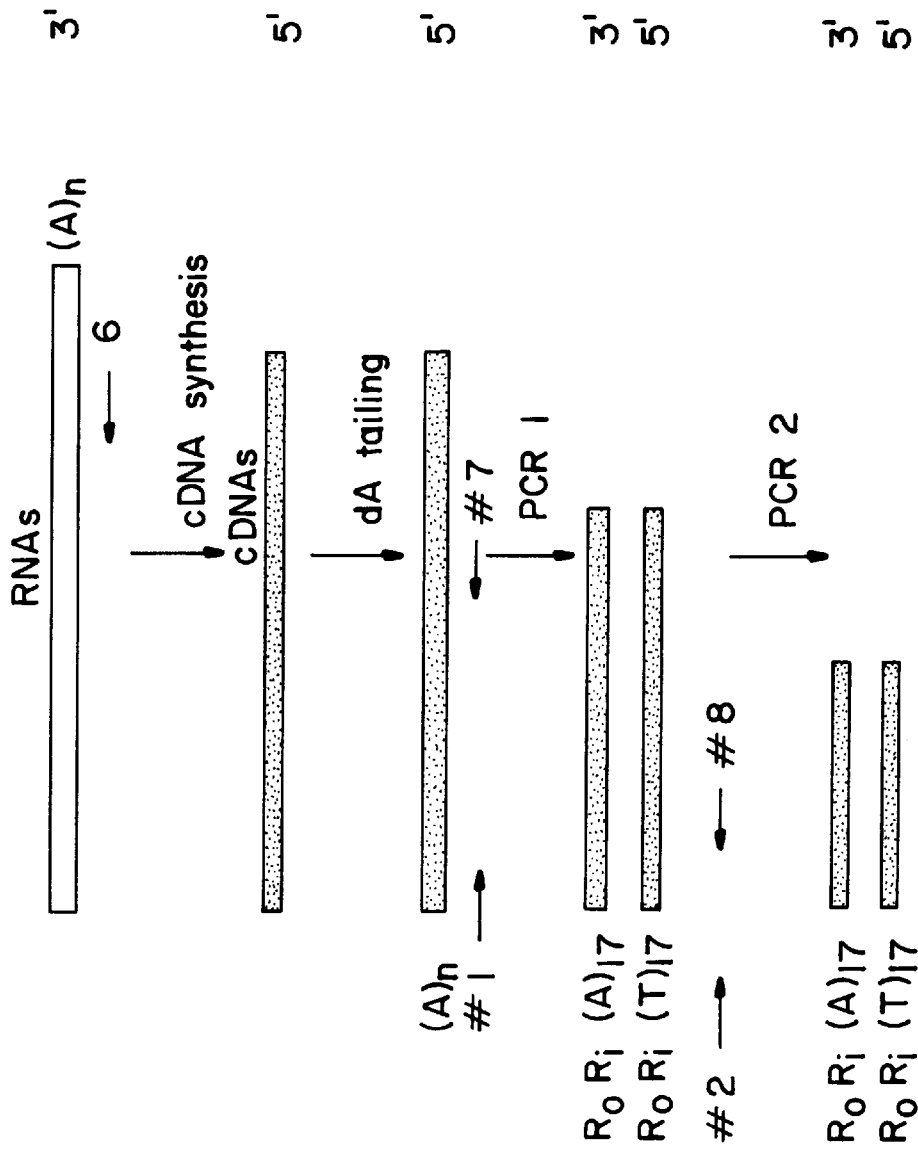

FIG. 4

| | | |
|---|---|---|
| Hu LPL | YPVSAGYTKLVGQDVARFINWMEEEFNYPLDNVHLLGYSLGAHAAGIAG | 169 |
| Mo LPL | YPVSAGYTKLVGNDVARFINWMEEEFNYPLDNVHLLGYSLGAHAAGVAG | 161 |
| Hu HL  | YTIAVRNTRLVGKEVAALLRWLEESVQLSRSHVHLIGYSLGAHVSGFAG | 178 |
| Mo HL  | YTQASYNTRVLGAEIAFLVQVLSTEMGYSPENVHLIPHSLGSHVAGEAG | 180 |
| Dm PLA | YKAAVGNTRLVGNFIAMIAKKLVEQYKVPMTNIRLVGHSLGAHISGFAGK | 148 |
| P+L    | Y   G T LVG   A       E     P  N   L G SLGAH  G AG | |
| P+H    | Y  AV NTRLVG   A       E             L G SLGAH SGFAG | |

| | | |
|---|---|---|
| Hu LPL | SLTNKKVNRITGLDPAGPNFEYAEAPSRLSPDDADFVDVLHT FTRG | 215 |
| Mo LPL | SLTNKKVNRITGLDPAGPNFEYAEAPSRLSPDDADFVDVLHT FTRG | 207 |
| Hu HL  | SSIGGTHKIGRITGLDAAGPLFEGSAPSNRLSPDDANFVDAIHT FTRE | 226 |
| Mo HL  | RRLEGHVGRITGLDPAEPCFQGLPEEVRLDPSDAMFVDVIHTDSAPI | 227 |
| Dm PLA | RVQELKLGKFSEIIGLDPAGPSFKKNDCSERICETDAHYVQILHT | 193 |
| P+L    |         K   I GLDPAGP F        R     DA V  LHT | |
| P+H    |         K   I GLD AGP F    S R     DA V   HT | |

| | | |
|---|---|---|
| Hu LPL | SPGRSIGIQKPVGHVDIYPNGGTFQPGC | 243 |
| Mo LPL | SPGRSIGIQKPVGHVDIYPNGGTFQPGC | 235 |
| Hu HL  | HMGLSVGIKQPIGHYDFYPNGGSFQPGC | 254 |
| Mo HL  | IPYLGFGMSQKVGHLDFFPNGGKEIPGC | 255 |
| Dm PLA | SSNLGTERTLGTVDFYINNGSNQPGC | 219 |
| P+L    |        G       G VD Y N G  QPGC | |
| P+H    |        G       G  DFY N GS QPGC | |

FIG. 5A

```
ATTTCCGGGTAAGTTTGTGTACGTTCTCACACAAACAAAATCATGAAGAAAATATGA                    60

ATTTAAAGTATTTATTATTCGTGTATTTGTGCAAGTGTAAATTGTGCTATGGAC                       120

G   P   K   C   P   F   N   S   D   T
ATGGTGATCCGTTATCTTACGAATTAGATAGAGGACCCAAATGTCCTTTTAATTCTGATA                 180

V   S   I   I   E   T   R   E   N   R   N   R   D   L   Y   T   L   Q   T
CAGTTTCGATAATTATTGAAACAAGGGAAAACCGAAATCGTGATCTTTATACACTACAGA                 240

L   Q   N   H   P   E   F   K   K   K   T   I   T   R   P   V   V   F   I   T
CATTACAGAATCATCCTGAATTTAAGAAAAAGACTATAACACGTCCAGTGTATTCATTA                  300

H   G   F   T   S   S   A   S   E   T   N   F   I   N   L   A   K   A   L   V
CACATGGTTTTACTTCATCTGCAAGTGAAACAAATTTCATAAATTTAGCAAAAGCTTTGG                 360

D   K   D   N   Y   M   V   I   S   I   D   W   Q   T   A   C   T   N   E
TAGATAAAGATAACTATATGGTTATCTCAATCGATTGGCAGACGCGTGCTTGTACTAATG                 420

A   A   G   L   K   Y   L   Y   Y   P   T   A   A   R   N   T   R   L   V   G
AAGCTGCAGGTTTAAAGTATTTATATTATCCTACTGCTGCTAGAAATACACGTTTAGTTG                 480

Q   Y   I   A   T   I   T   Q   K   L   V   K   H   Y   K   I   S   M   A   N
GACAATATATCGCTACGATTACCCAGAAACTCGTAAAACACTATAAAATCTCGATGGCAA                 540

I   R   L   I   G   H   S   L   G   A   H   A   S   G   F   A   G   K   K   V
ATATACGATTAATTGGACATAGCTTAGGAGCACATGCTTCAGGTTTTGCAGGCAAAAAGG                 600

Q   E   L   K   L   G   K   Y   S   E   I   I   G   L   D   P   A   R   P   S
TTCAAGAGTTAAAATTAGGAAAATATTCTGAAATTATTGGGCTTGATCCTGCTAGGCCTT                 660
```

FIG. 5B

```
       F   D   S   N   H   C   S   E   R   L   C   E   T   D   A   E   Y   V   Q   I
CGTTCGATTCAAATCATTGTTCCGAAAGACTCTGCGAGACAGATCGAGAATATGTTCAAA                           720

I   H   T   S   N   Y   L   G   T   E   K   T   L   G   T   V   D   F   Y   M
TTATACATACATCAAACTATTAGGAACCGAAAAAACCCTTGGTACCGTCGATTTCTACA                             780

N   N   G   K   N   Q   P   G   C   G   R   F   F   S   E   V   C   S   H   S
TGAATAACGGAAAGAATCAACCTGGTTGCGGTAGATTTTTCTCAGAAGTTTGCTCTCATT                            840

R   A   V   I   Y   M   A   E   C   I   K   H   E   C   C   L   I   G   I   P
CGAGAGCCCGTGATATACATGGCTGAGTGCATAAAAACACGAATGTGTTAATTGGGATAC                            900

K   S   K   S   S   Q   P   I   S   C   T   K   Q   E   C   V   C   V   G
CGAAGTCAAAGAGTTCGCAGCCTATTCGTGTGCACAAAACAGGAGTGCGTTTGCGTTG                              960

L   N   A   K   K   Y   T   S   R   G   S   F   Y   V   P   V   E   S   T   V
GATTAAAACGCAAAGAAGTATACTAGTAGAGGCTCATTTATGTACCGGTTGAAAGTACTG                            1020

P   F   C   N   N   K   G   K   I   I   *
TTCCTTTTTGCAATAACAAGGGGAAGATAATTTAATAATAATAAAAAGTAATTTCCATTC                            1080

ATCGAAATGCATTTGTTAATGGTGAATGAATAATTACCATTTAACAATAATCGTACAT                              1140

GCAGAATGTCGTCCAAATAATTGCGGAGTATATAATGGATGATCTTAGCAAATTTAAAA                             1200

AATAAAAAGAATTATATAAACATATACCCTATTTGATTTGCTTTTTAGTTGTAGTGAAT                             1260

TGAATTTTTCTGTCTGCTTAATTTGAAACTGCTTCCTTGCTTCTGAATAAATGCCTGTAA                            1320

ACATAAAAAAAAAAAAAAAA                                                                    1341
```

FIG. 6A

```
  Y   I   Y   H   H   R   *   H   L   P   P   N   F   S   R   S   N   C   E   K
TATATATATCACCACCGATGACACTCCCGCCTAACTTTCCAGATCGAATGCGAAAAA                         60

S   E   R   P   K   R   V   F   N   I   Y   W   N   Y   P   T   F   M   C   H    20
TCCGAGAGACCGAAAAGAGTCTTCAACATTATGGAACGTTCCTACCTTATGTGTCAT                        120

Q   Y   G   L   Y   F   D   E   V   T   N   F   N   I   K   H   N   S   K   D    40
CAGTATGGCCTATACTTCGACGAGGTTACAAATTTAATATAAGCATAATTCTAAGGAC                       180

D   F   Q   G   D   K   I   S   I   F   Y   D   P   G   E   F   P   A   L   L    60
GATTTCCAGGGTGACAAGATCTCAATTTTTTATGATCCTGGAGAATTCCCGGCATTGTTG                     240

P   L   K   E   G   N   Y   K   I   R   N   G   G   V   P   Q   E   G   N   I    80
CCGCTCAAAGAAGGCAATTATAAGATAAGAAACGGAGAGTTCCTCAAGAAGTAACATA                       300

T   I   H   L   Q   R   F   I   E   N   L   D   K   T   Y   P   N   R   N   F   100
ACGATACATCTCCAAAGATTTATCGAAAATTTGGATAAACATATCCAATAGGAACTTC                       360

N   G   I   G   V   I   D   F   E   R   W   R   P   I   F   R   Q   N   W   G   120
AACGGTATCGGTGTGATCGACTTTGAAAGATGGAGACCGATCTTCCGACAAAATTGGGGC                     420

N   M   M   I   H   K   K   F   S   I   D   L   V   R   N   E   H   P   F   W   140
AATATGATGATTCATAAGAAGTTTCAATAGACCTAGTTCGCAATGAACATCCATTCTGG                      460

D   K   K   M   I   E   L   E   A   S   K   R   F   E   K   Y   A   R   L   F   160
GATAAAAAGATGATCGAATTGGAGGCATCTAAGAGGTTTGAAAATATGCCAGACTTTTC                      540
```

FIG. 6B

```
  M  E  E  T  L  K  L  L  A  K  K  T  R  K  Q  A  D  W  G  Y  Y        180
ATGGAGGAAACTTTGAAATTGCCAAAAGACTAGGAAGCAGGCCGATTGGGGCTATTAC              600

G  Y  P  Y  C  F  N  M  S  P  N  N  L  V  P  D  C  D  A  T           200
GGATATCCCTACTGTTTTAATATGTCGCCTAATAATCTCGTACCCGATGTGACGCTACA             660

A  M  L  E  N  D  K  M  S  W  L  F  N  N  Q  N  V  L  L  P           220
GCGATGCTCGAGAACGACAAGATGTCGTGGCTGTTCAATAATCAAAATGTACTTCTACCA            720

S  V  Y  I  R  H  E  L  T  P  D  Q  R  V  G  L  V  Q  G  R           240
TCCGTCTATATTAGACACGAACTGACCCCTGATCAAAGAGTGGTTAGTCCAAGGAAGA              780

V  K  E  A  V  R  I  S  N  N  L  K  H  S  P  K  V  L  S  Y           260
GTGAAGGAAGCTGTTAGGATATCGAATAATTAAAACATTCACCGAAAGTGCTCTCTTAT             840

W  W  Y  V  Y  Q  D  D  T  N  T  F  L  T  E  T  D  V  K  K           280
TGGTGGTACGTGTATCAGGACGATACAAACACTTTTCTTACCGAGACCGACGTGAAAAAG            900

T  F  Q  E  I  A  I  N  G  G  D  G  I  I  W  G  S  S  S              300
ACTTTCCAAGAGATAGCGATTAACGGTGGGGATGGTATCATTATATGGGGTAGCTCGTCC            960

D  V  N  S  L  S  K  C  K  R  L  R  E  Y  L  L  T  V  L  G           320
GACGTAAACAGCTTAAGTAAATGTAAGAGATTACGGGAGTATCTGTTGACGGTTTGGGA            1020

P  I  T  V  N  V  T  E  T  V  N  *                                   331
CCAATCACGGTTAACGTGACGGAAACCGTCAACTAAAGATTATCCCTAAACTTTTAGTAC           1080

AATCTATGTAACCTCTGCCGATGGCGATAGTGTGTTCAATGATCGCTTTGCGAACGC              1140

TATCGATGCTGCAACGATGAATACTGCGACAATGCCATCACATTGAAAAGACTTTTCGCA           1200

GGAAGGAAAAAAAAAAAAAAAAAAAAAAAAAAA                                     1229
```

FIG. 7A

```
bee      PDNNKTVREFNVYWNVPTFMCHKYGLRFEEVSEKYGILQNWMDKFRGEEI    50
hornet   SERPKRVFNIYWNVPTFMCHQYGLYFDEVTN-FNIKHNSKDDFQGDKI     47
g. pig   APPLIPNVPLLWVWNAPTEPCIGGTNQPLDMSF-FSIVGTPRKNITGQSI    52 bee      AILYDPGMFPALLKDPN-GNVVARNGGVPQLGNLTKHLQVFRDHLINQIP    99
hornet   SIFYDPGEFPALLPLKE-GNYKIRNGGVPQEGNITIHLQRFIENLDKTYP    96
g. pig   TLYYVDRLGYYPYIDPHTGAIV--HGGLPQLMNLQQHLRKSRQDILFYMP   100 bee      DKSFPGVGVIDFESWRPIFRQNWASLQPYKKLSVEVVRREHPFWDDQRVE   149
hornet   NRNFNGIGVIDFERWRPIFRQNWGNMMIHKKFSIDLVRNEHPFWDKKMIE   146
g. pig   TDSV GLAVIDWEEWRPTWYRNWRPKDIYRNKSIELVKSQHPQYNHSYAV   149
```

FIG. 7B

```
bee     ......•.••.••.•.••  •  .•..••.••.        •
        QEAKRRFEKYGQLFMEETLKAAKRMRPAANWGYYAYPYCYNLTPNQPS  197
hornet  LEASKRFEKYARLFMEETLKLAKTTRKQADWGYYGYPYCFNMSPNNLV   194
g. pig  AVAKRDFERTGKAFMLETLKLGKSLRPSSLWGYYLFPDCYNTHFTKPNYD 199
              •                •       •  •••• bee     •.•.•.••.••  ...••.••.•  •                 ......
        AQCEATTMQENDKMSWLFESEDVLLPSVYLRWNLTSGERVGL VGGRVKE 246
hornet  PDCDATAMLENDKMSWLFNNQNVLLPSVYIRHELTPDQRVGL VQGRVKE 243
g. pig  GHCPPIELQRNNDLQWLWNDSTALYPSVYLTSRVRSSQNGALYVRNRVHE 249
              •                •                    • bee     •  .•.••.••  •                          •
        ALRIARQMTTSRKKVLPYYWYK---YQDRRDTDLSRADLEATLRKITDLG 293
hornet  AVRISNNLKHSP-KVLSYWWYV---YQDDTNTFLTETDVKKTFQEIAING  289
g. pig  SIRVSKLMDD--KNPLPIYVYIRLVFTDQTTFLELDDLVHSVGEIVPLG   297
              •                                       • bee     •  .•.••.••  •                                •
        ADGFIIWGSSDDINTKAKCLQFREYLNNELGPAVKRIALNNNANDRLTVD 343
hornet  GDGIIWGSSSSDVNSLSKCKRLREYLLTVLGPITVNVTETVN        331
g. pig  VSGIIWGSLSLTRSLVSCIGLENYMKGTLLPYLINVTLAAKMCGQVLCK  347
              •                                            •
```

CLONING AND RECOMBINANT PRODUCTION OF VESPID VENOM HYALURONIDASES, AND IMMUNOLOGICAL THERAPIES BASED THEREON

The present invention is a Division of application Ser. No. 08/180,209 filed Jan. 11, 1994, now U.S. Pat. No. 5,593,877 which is a continuation-in part of application Ser. No. 08/031,400, filed Mar. 11, 1993, now abandoned, of which the instant Application claims the benefit of the filing date under 35 U.S.C. § 120, and the disclosure of which is incorporated herein by reference in its entirety.

FIELD OF THE INVENTION

The present invention is directed to nucleic acids encoding vespid venom allergens, in particular venom enzymes such as phospholipase and hyaluronidase, or fragments thereof, recombinant vectors comprising such nucleic acids, and host cells containing the recombinant vectors. The invention is further directed to expression of such nucleic acids to produce a recombinant vespid venom enzyme, such as phospholipase or hyaluronidase, or recombinant fragments thereof. Such an allergen and fragments thereof are useful for diagnosis of allergy and for therapeutic treatment of allergy.

BACKGROUND OF THE INVENTION

Biochemical Aspects of Insect Venom Allergens

Insect sting allergy to bees and vespids is of common occurrence. The vespids include hornets, yellowjackets and wasps (Golden, et al., 1989, Am. Med. Assoc. 262:240). Susceptible people can be sensitized on exposure to minute amounts of venom proteins; as little as 2–10 µg of protein is injected into the skin on a single sting by a vespid (Hoffman and Jacobson, 1984, Ann. Allergy. 52:276).

There are many species of hornets (genus Dolichovespula), yellowjackets (genus Vespula) and wasp (genus Polistes) in North America (Akre, et al., 1980, "Yellowjackets of America North of Mexico," Agriculture Handbook No. 552, US Department of Agriculture). The vespids have similar venom compositions (King, et al., 1978, Biochemistry 17:5165; King, et al., 1983, Mol. Immunol. 20:297; King, et al., 1984, Arch. Biochem. Biophys. 230:1; King, et al., 1985, J. Allergy and Clin. Immunol. 75:621; King, 1987, J. Allergy Clin. Immunol. 79:113; Hoffman, 1985, J. Allergy and Clin. Immunol. 75:611). Their venom each contains three major venom allergens, phospholipase (37 kD), hyaluronidase (43 kD) and antigen 5 (23 kD) of as yet unknown biologic function.

In addition to the insect venom allergens described above, the complete amino acid sequence of several major allergens from different grass (Perez, et al., 1990, J. Biol. Chem. 265:16210; Ansari, et al., 1989, Biochemistry 26:8665; Silvanovich, et al., 1991, J. Biol. Chem. 266:1204), tree pollen (Breiteneder, 1989, EMBO J. 8:1935; Valenta, et al., 1991, Science, 253:557), weed pollen (Rafnar, et al., 1991, J. Biol. Chem. 266:1229; Griffith, et al., 1991, Int. Arch. Allergy Appl. Immunol. 96:296), mites (Chua, et al., 1988, J. Exp. Med. 167:175), cat dander (Griffith, et al., 1992, Gene. 113:263), and mold (Aruda, et al., 1990, J. Exp. Med. 172:1529; Han, et al., 1991, J. Allergy Clin. Immunol. 87:327) have been reported in the past few years. These major allergens are proteins of 10–40 kD and they have widely different biological functions. Nearly all allergens of known sequences have a varying extent of sequence similarity with other proteins in our environment.

T and B Cell Epitopes of Allergens

Antibody responses to proteins require the collaboration of T helper and B lymphocytes and antigen presenting cells (APC). The antigen receptors of B cells are the membrane-bound antibody (Ab) molecules, which recognize and bind immunogens directly. The antigen receptors of T cells (TCR) only recognize and bind complexes of antigenic peptide-MHC class II molecule. Immunogens are first processed by APC into peptides that are presented on the surface of APC in association with the MHC class II molecules (Unanue, 1992, Current Opinion in Immunol 4:63). As MHC molecules are highly polymorphic in individuals, they have different specificity of binding antigenic peptides (Rothbard and Gefter, 1991, Ann. Rev. Immunol. 9:527). This is one mechanism for genetic control of immune response.

T helper cells are activated when the antigen receptor binds the peptide-MHC complex on the surface of APC. Activated T cells secrete lymphokines. In mice (Street and Mosmann, 1991, FASEB J. 5:171) and apparently in humans (Wierenga, et al., 1990, J. Immunol. 144:4651; Parronchi, et al., 1991, Proc. Natl. Acad. Sci. USA. 88:4538) the T helper cells can be divided into different types on the basis of their patterns of lymphokine production. Primarily, T helper cells divide into two groups: TH1 cells producing IL-2 and IFN-γ, and TH2 cells producing IL-4 and IL-5. These lymphokines in turn influence the antigen-activated B cells to differentiate and proliferate into plasma cells secreting Abs of different isotypes. IL-4 is one lymphokine known to influence IgE synthesis (Finkelman, et al., 1990, Ann. Rev. Immunol. 8:303).

It is believed that the entire accessible surface of a protein molecule can be recognized as epitopes by the antigen receptors of B cells, although all epitopes are not necessarily recognized with equal likelihood (Benjamin, et al., 1984, Ann. Rev. Immunol. 2:67). B cell epitopes of a protein are of two types: topographic and linear. The topographic type consists of amino acid residues which are spatially adjacent but may or may not be sequentially adjacent. The linear type consists of only sequentially adjacent residues. X-ray crystallographic data of Ag-Ab complexes indicate the size of their complementary binding region to have 16–17 amino acid residues (Amit, et al., 1986, Science 233:747), but peptide mapping suggests that less than about 8 residues contribute significantly to the binding process of a linear epitope (Appel, et al., 1990, J. Immunol. 144:976).

Allergens, like other protein antigens, can have both types of B cell epitopes or only one. For example, vespid antigen 5s have both types. Bee venom melittin appears to have only one B cell epitope of linear type (King, et al., 1984, J. Immunol. 133:2668).

T cell epitopes of proteins consist of only the linear type since they are peptides that have been processed in the lysosomes of APC by proteases of unknown specificity (Unanue, 1992, Curr. Op. Immunol. 4:63). Analysis of naturally processed antigenic peptides bound to MHC class II molecules indicates that their size ranges from about 13 to 17 amino acid residues, but analysis of synthetic peptide-MHC class II molecule complex for their T cell proliferate response suggests a minimal size of about 8 amino acid residues (Cf. Rudensky et al., 1991, Nature 353:622). Studies suggest that T cell epitopes are distributed throughout the entire protein molecule, and they may function as major or minor determinants depending on the MHC haplotype of the immunized host (Roy, et al., Science 244:572; Gammon, et al., 1987, Immunol. Rev. 98:53; O'Hehir et al., 1991, Ann. Rev. Immunol. 9:67).

Hypersensitivity of the immediate type is known to be caused by the presence of allergen-specific IgE. IgE is found in the circulation and bound to specific IgE-Fc receptors on mast cells and basophils. Cross-linking of cell-bound IgE by allergens leads to release of histamine, leukotrienes and other chemical mediators that cause the allergic symptoms. IgE is one of the different isotypes of immunoglobulins. As pointed out above, lymphokines secreted by T cells influence isotype switch events in B cells.

Because of the central role of TH2 cells in determining the isotypes switch event of B cells, the T cell epitopes of several allergens have been mapped (Cf. O'Hehir et al., supra). These allergens include ragweed Amb α III, rye grass Lol p I, cat Fel d I, mouse urine Mus m I, midge Chi t I, bee venom phospholipase $A_2$ (Dhillon, et al., 1992, J. Allergy Clin. Immunol. 90:42) and melittin (Fehlner, et al., 1991, J. Immunol. 146:799). The data do not reveal any unusual or common structural features. However, any conclusion from these data is qualified as these data are collected from humans and mice of different haplotypes.

Modulation of T and B Cell Responses

Normally hosts are tolerant to the dominant B and T cell epitopes of self proteins by clonal deletion and anergy. However this tolerance can be broken under certain circumstances (Gammon, et al., 1991, Immunol. Today. 12:193; Basten, et al., 1991, Immunol. Rev. 122:5). It has been suggested that self-tolerance is broken in autoimmune diseases through encounters with foreign proteins that are similar to host proteins. Therefore the sequence similarity of allergens with autologous proteins is of interest for closer investigation.

Mature B cells are activated in response to multi-valent antigens which can cross-link cell surface Ig receptors (DeFranco, 1987, Ann. Rev. Cell Biol. 3:143), and they are rendered anergic in response to mono-valent antigen (Basten, et al., 1991, supra). Antigen activation of T cells requires not only the integration of TCR with peptide-MHC complex but also with other co-stimulating signals on the surface of APC (Schwartz, 1990, Science 248:1349; Jenkins and Miller, 1992, FASEB J. 6:2428). Interaction of TCR with peptide-MHC complex in absence of co-stimulating signals can lead to T cell anergy.

The molecular mechanism of B or T cell anergy is not yet understood (Cf. Schwartz, 1990, supra; Jenkins and Miller, 1992, supra; Ales-Martinez, et al., 1991, Immunol. Today 12:201). In vitro studies with T cell clones reveals that occupancy of TCR by artificial peptide-MHC complex in absence of co-stimulating signals leads to altered intracellular signal transduction and/or repressor gene activation which can prevent lymphokine transcription.

Early studies have shown that the physical state of the immunogen and the route of immunization are important variables in determining the outcome of an immune response. In the light of our current understanding, these variables may well influence antigen presentation so as to have T and B cell activation or anergy.

One way to treat allergic diseases is by immunotherapy which involves repeated subcutaneous injections of the offending allergen(s) into patients. The amounts of allergens which can be injected are limited by the danger of unwanted systemic allergic reaction in patients. For most patients following immunotherapy, their allergen-specific IgE levels initially rise followed with gradual decrease of their allergen-specific IgE levels, and there is also downregulation of allergen-specific T cell responses (P. S. Norman, 1993, Current Op. Immunol. 5:968).

Because of the undesirable systemic reaction on immunotherapy with native allergens, there has been continued interest in the development of modified allergens with reduced allergenic activities for immunotherapy (T. P. King, 1993, in "Bronchial Asthma," edited by E. B. Weiss and M. Stein, Little Brown, Boston, pp. 43–49; R. E. O'Hehir et al., 1991, supra).

Two reports have appeared recently on the use of T cell epitope peptides to modulate allergen-specific immune responses. One report is on the subcutaneous injection of mice with two peptides from the major cat allergen Fel d I to decrease T cell response to the entire molecule Fel d I (Briner et al., 1993, Proc. Natl. Acad. Sci. U.S.A. 90:7608–12). Another is on the intranasal therapy with a peptide from the major mite allergen Der p I to suppress allergen-specific response in naive or sensitized mice (Hoyne et al., 1993, J. Exp. Med. 178:1783–1788).

Since an MHC class II molecule of any one haplotype can bind a wide range of peptides in its binding groove, it may be possible to modulate T cell response by inhibition of allergen-derived T cell epitope binding to MHC molecules with other peptides. For example, a mouse lysozyme peptide which is not immunogenic by itself in H-$2^k$ mice inhibits T cell response to hen egg white lysozyme (Adorini and Nagy, 1990, Immunol. Today. 11:21). Another example is the in vitro inhibition of T cell response to a mite allergen by an influenza HA peptide (O'Hehir et al., 1991, J. Allergy Clin. Immunol. 87:1120).

Experimental autoimmune encephalomyelitis (EAE) in mice or rats is a well-studied model for multiple sclerosis. Many studies have identified immunodominant T cell determinants for myelin basic protein, which is used to induce this condition. Peptides that correspond to immunodominant epitopes of myelin basic protein can induce tolerance to the same peptide antigen or to the intact myelin basic protein. The same peptides that induced tolerance could also induce T cell anergy in an ongoing autoimmune response (Gaur et al., 1992, Science 259:1491–1494).

Immune response to an immunogen/allergen depends in part on the genetic make-up of the host, the route and mode of immunization and the immunogen/allergen. The extent to which a vespid venom allergen determines the outcome of IgE response is not known. How many B and T cell epitopes does each vespid venom allergen have? Are there immunodominant B or T cell epitopes of a vespid venom allergen recognized by different or all susceptible individuals? Are there T cell epitopes which favor IgE class switch events in B cells? Does antigenic cross reactivity of vespid venom allergens with host proteins play a role as to why some proteins are more allergenic than others are? Can tolerance to a multi-valent vespid venom allergen be induced by treatment with a single or a combination of B or T cell epitopes?

Thus, there is a need in the art to delineate the B and helper T cell epitopes of major vespid venom allergens. There is a particular need to delineate the B and helper T cell epitopes of the vespids hornet (e.g., *Dolichovespula arenaria*), yellowjacket (e.g., *Vespula vulgaris*) and wasp (e.g., *Polistes annularis*). In particular, the major vespid venom allergens phospholipase and hyaluronidase are appropriate targets for determining the important B and T cell epitopes. In order to fully address the basis for allergic response to vespid allergens, and to develop allergen-based immunotherapies, the cDNA and protein sequences of several homologous allergens need to be investigated. Moreover, vectors suitable for high level expression in bacteria and eukaryotic cells of vespid allergens or their fragments should be developed. Recombinant vespid allergens and their fragments may then be used to map their B and T cell epitopes in the murine and, more importantly, human systems by antibody binding and T cell proliferation tests, respectively.

There is a further need to determine whether there is cross reaction of the T and B cell epitopes of vespid allergens with other environmental and/or autologous proteins. Thus there is a need to determine whether vespid allergens share partial identity with other environmental proteins, especially with autologous proteins, and more importantly, to obtain the sequences of the regions of the partial identity, in particular the specific amino acid sequences of such regions of partial identity. There is a further need to determine the level of cross reactivity of vespid allergens with other proteins at the B cell and T cell level, the relevance of this cross reactivity, and whether such cross reactivity is pathological, i.e., involved in or responsible for allergy, or beneficial, i.e., inhibitory of allergy.

There is also a need in the art to use peptides having T or B cell epitopes of vespid venom allergens to study induction of tolerance in mice and induction of tolerance in humans.

There is a further need to test whether a modified peptide inhibits allergen T cell epitope binding to MHC class II molecule, or induces T cell anergy, or both.

Thus, there is a need in the art for the sequence information about vespid venom allergens, and a plentiful source of such allergens for immunological investigations and for immunological therapy of the allergy.

The citation of references herein shall not be construed as an admission that such is prior art to the present invention.

SUMMARY OF THE INVENTION

The present invention provides nucleic acids encoding vespid venom enzymes, in particular phospholipases and hyaluronidases, and immunomodulatory fragments, derivatives or analogs thereof. In particular, the invention is directed to nucleic acids encoding vespid venom phospholipases, for example, *Dolichovespula maculata* phospholipase and *Vespula vulgaris* phospholipase, and to vespid venom hyaluronidase, for example, *D. maculata* hyaluronidase. In specific embodiments, a nucleic acid of the invention encodes an immunomodulatory portion of a T cell epitope of a vespid venom enzyme, such as phospholipase or hyaluronidase. In another specific embodiment, a nucleic acid of the invention encodes an antigenic portion of a B cell epitope of a vespid venom enzyme, such as phospholipase or hyaluronidase. Expression of the nucleic acids of the invention provides a plentiful source of the vespid enzymes for diagnosis and therapy.

It is a particular advantage of the present invention that the nucleic acid sequences encoding a number of vespid venom enzymes, in particular phospholipases and hyaluronidase, are provided. Such nucleic acid sequences allow deduction of the amino acid sequence of the vespid venom enzymes. Knowledge of the amino acid sequence allows for the determination of relevant T cell and B cell epitopes of an enzyme. More importantly, the immunodominant T cell and B cell epitopes can be determined for each enzyme allergen-sensitive individual or group of individuals, i.e., who share a susceptible MHC haplotype, or for whom the T cell epitope favors class switch events to IgE class antibodies. Once such T cell and B cell epitopes are determined, it is possible to devise immunological therapies for vespid venom enzyme-specific allergic conditions, e.g., for sensitivity to vespid venom phospholipase or hyaluronidase, or both.

Thus, the instant invention further provides polypeptides encoded by the nucleic acids of the invention. In particular, the invention provides polypeptides having an immunomodulatory portion of a T cell epitope of the vespid venom enzyme, e.g., phospholipase or hyaluronidase. In another embodiment, the invention provides polypeptides having an antigenic portion of a B cell epitope of the vespid venom enzyme, e.g., phospholipase or hyaluronidase. More particularly, the invention provides such polypeptides of a vespid venom phospholipase, for example, *Dolichovespula maculata* phospholipase and *Vespula vulgaris* phospholipase A1, as well a polypeptides of a vespid venom hyaluronidase, for example, *D. maculata* hyaluronidase.

The present invention further provides expression vectors comprising the nucleic acids of the invention operationally associated with a promoter. The present invention also provides methods for producing the vespid venom enzymes, e.g., phospholipases or hyaluronidases, encoded by the nucleic acids of the invention. In particular, the invention provides for culturing a cell transformed with an expression vector of the invention so that the vespid venom enzyme, e.g., phospholipase or hyaluronidase, is expressed by the cell, and recovering the vespid venom enzyme so expressed from the culture. More particularly, the invention provides for expression of expression vectors comprising nucleic acids encoding a vespid venom phospholipase, for example, *Dolichovespula maculata* phospholipase and *Vespula vulgaris* phospholipase A1, or a vespid venom hyaluronidase, for example, *D. maculata* hyaluronidase, or fragments, derivatives or analogs thereof.

In yet another embodiment, the present invention provides a pharmaceutical composition effective for the treatment of a vespid venom allergen-specific allergic condition comprising a polypeptide of the invention that has an immunomodulatory portion of a T cell epitope of a vespid venom enzyme, e.g., phospholipase or hyaluronidase, or an antigenic portion of a B cell epitope of a vespid venom enzyme, e.g., phospholipase or hyaluronidase. More particularly, the invention provides pharmaceutical compositions comprising such polypeptides of a vespid venom phospholipase, for example, *Dolichovespula maculata* phospholipase and *Vespula vulgaris* phospholipase, or a vespid venom hyaluronidase, for example, *D. maculata* hyaluronidase.

In yet still another embodiment, the present invention provides a method for treating a vespid venom allergen-specific condition comprising administering a therapeutically effective dose of a pharmaceutical composition of the invention.

Thus, an advantage of the invention is that it provides for production of many vespid venom enzymes, in particular phospholipases and hyaluronidases, which can be used therapeutically for the treatment of vespid venom enzyme-specific allergic conditions. Most importantly, the therapeutic treatment can be highly specific and individualized, since the invention allows production of a vespid venom enzyme polypeptide that has immunomodulatory activity in any individual or group of individuals.

It is another particular advantage of the present invention to have the nucleic acid sequences and deduced amino acid sequences of a large number of various vespid venom enzyme, in particular phospholipases and hyaluronidases, from different species of vespids to allow comparison of the homology of analogous enzymes between species. This information provides a basis for evaluating cross-reactivity of the allergens, which can be important for allergic reactions and for therapeutic treatments.

It is a further advantage of the present invention that the degree of similarity of many vespid venom enzymes, in particular phospholipases and hyaluronidases, to environmental proteins and/or autologous proteins can be evaluated. It is believed that similarity of the vespid venom enzymes to such environmental proteins, and particularly to autologous proteins, has important implications for the allergic response.

ABBREVIATIONS

| | | |
|---|---|---|
| Dol m | *Dolichovespula maculata* | white face hornet |
| Dol a | *D. arenaria* | yellow hornet |
| Pol a | *Polistes annularis* | wasp |
| Pol e | *P. exclamans* | wasp |
| Ves m | *Vespula maculifrons* | yellowjacket |
| Ves v | *V. vulgaris* | yellowjacket |
| PCR | | polymerase chain reaction |
| RACE | | rapid amplification of cDNA ends |
| TCR | | T cell receptor for antigen |

BRIEF DESCRIPTION OF THE DRAWINGS

FIG. 1. cDNA (SEQ ID NO:16) and amino acid (SEQ ID NO:17) sequences of hornet phospholipase (Dol m I). Nucleotide and amino acid positions are numbered on the right. Numbering of amino acid residues begins and ends at the N- and C-termini of phenylalanine and isoleucine, respectively, corresponding to nucleotide positions of 52–54 and 949–951; these amino acid residues and nucleotides are shown in bold characters. The underlined amino acid residues were also established by Edman degradation of CNBr peptides.

FIG. 4. Sequence similarity of Dol m I and mammalian lipases. Amino acid positions are numbered on the right. Abbreviations used: Hu, human; Mo, mouse; LPL, lipoprotein lipase; HL, hepatic lipase; Dm, white face hornet; and PLA, phospholipase. P+L and P+H indicate residues of hornet phospholipase which are identical to human lipoprotein or hepatic lipases respectively. Hu LPL-SEQ ID NO:18; MoLPL-SEQ ID NO:19; Hu HL-SEQ ID NO:20; Mo hl-SEQ ID NO:21; Dm PLA-SEQ ID NO:22.

FIGS. 5A and 5B. cDNA (SEQ ID NO:26) and deduced amino acid (SEQ ID NO:27) sequence of yellowjacket phospholipase. Nucleotide positions are numbered on the right. Nucleotides 1–152 correspond to the 5'-untranslated region and leader sequence. Nucleotides 153–1052 encode the mature protein. Nucleotides 1053–1341 correspond to the 3'-untranslated region. Underlined portions of the amino acid sequence were also established by Edman degradation of CNBr peptides. Note that the N-terminal sequence of natural venom was found to be FPKCP . . . , but the N-terminus translated from the cDNA is G PKCP . . . .

FIGS. 6A and 6B. cDNA (SEQ ID NO:54) and amino acid (SEQ ID NO:55) sequences of hornet hyaluronidase (Dol m II). Nucleotide and amino acid positions are numbered on the right. Numbering of amino acid residues begins and ends at the N- and C-terminal residues serine and asparagine, respectively, corresponding to nucleotide positionS of 61–63 and 1051–1053, respectively. The underlined amino acid sequence was also established by Edman degradation.

FIGS. 7A and 7B. Sequence comparison of honey bee (SEQ ID NO:56) and hornet venom (SEQ ID NO:57) hyaluronidases and guinea pig sperm protein PH-20 (SEQ ID NO:58). Alignment starts with residue 1 for both hyaluronidases and residue 4 for PH-20. Bee venom hyaluronidase and PH-20 contain 349 and 495 residues respectively. Gaps, indicated by hyphens, were added to maximize sequence homology. The filled circles highlight the amino acid residues that are common to these proteins.

DETAILED DESCRIPTION OF THE INVENTION

Figure 2A:
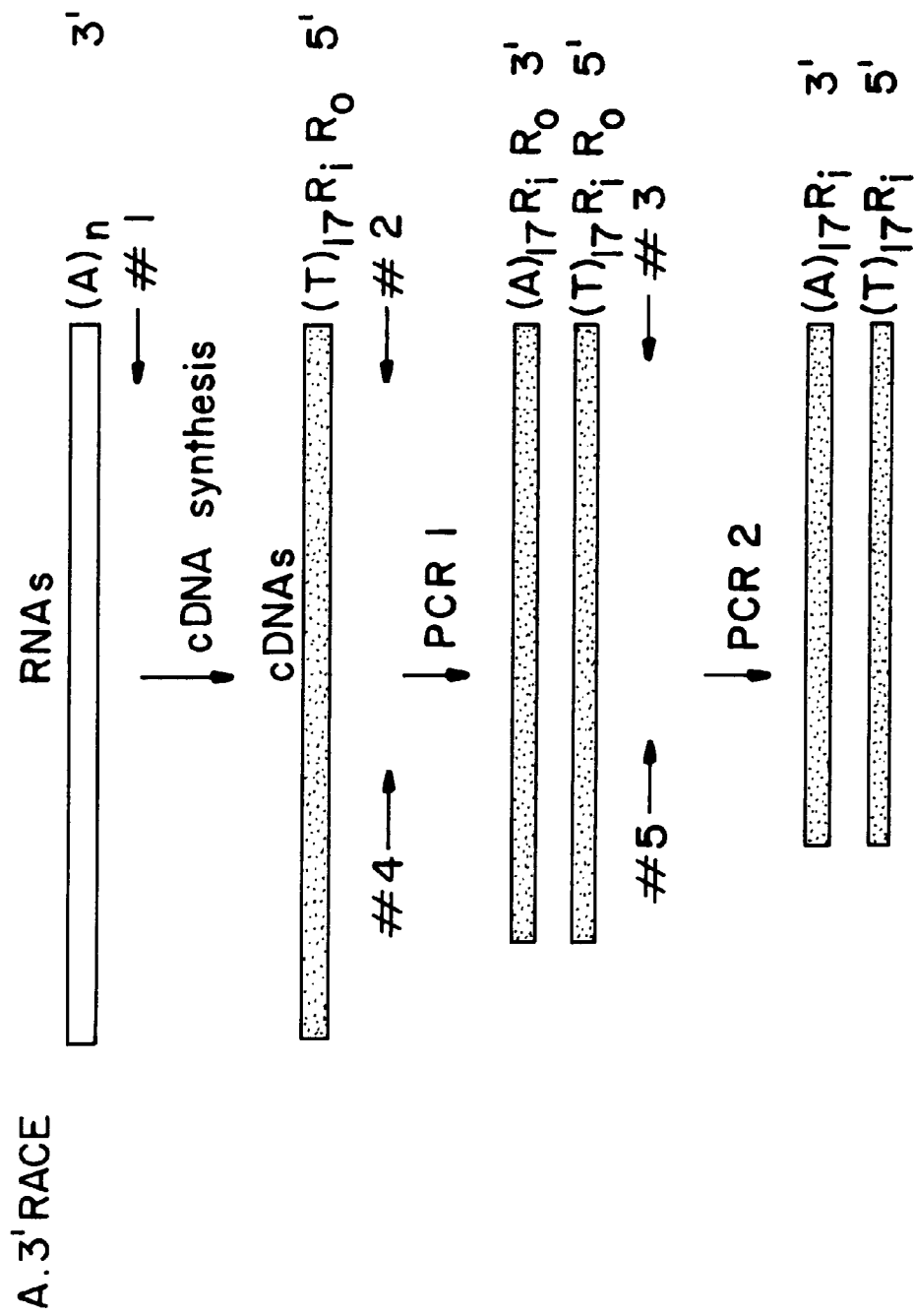
FIG. 2. Schematic diagram for rapid amplification of the 3' (A) and 5' (B) cDNA ends (RACE) of Dol m I. Open and solid bars represent RNA and DNA respectively. The oligonucleotide primers are numbered, and their sequences are given in Table 1.

The present invention is directed to recombinant nucleic acids encoding vespid venom enzymes, such as phospholipases and hyaluronidases, and immunomodulatory fragments, derivatives or analogs thereof, and polypeptides encoded by such nucleic acids useful in the diagnosis and therapy of vespid venom-specific allergy. In specific embodiments, the present invention is directed to a recombinant nucleic acid encoding an immunomodulatory fragment of a vespid phospholipase, in particular *Dolichovespula maculata* (white-face hornet) phospholipase (Dol m I) and *Vespula vulgaris* (yellowjacket) phospholipase (Ves v I), and an immunomodulatory fragment of a vespid venom hyaluronidase, in particular *D. maculata* hyaluronidase.

The invention is further directed to expression vectors comprising such nucleic acids, and to methods for producing vespid venom enzyme polypeptides of the invention by expressing such expression vectors and recovering the expressed vespid venom enzyme polypeptides.

The invention also provides pharmaceutical compositions effective for the treatment of a vespid venom allergen-specific allergic condition comprising a polypeptide of the invention, and methods for treating such allergic conditions comprising administering a therapeutically effective dose of the pharmaceutical compositions of the invention.

The polypeptides of the invention can also be useful for diagnosis of vespid venom-specific allergic conditions.

As used herein, the term "vespid venom allergen" refers to a protein found in the venom of a vespid, to which susceptible people are sensitized on exposure to the sting of the insect. While most antigens are characterized by being reactive with specific IgG class antibodies, an allergen is characterized by also being reactive with IgE type antibodies. The IgE type antibodies are responsible for mediating the symptoms of an allergic condition, i.e., immediate-type hypersensitivity.

As herein, the term "vespid" is used according to the practice of those in he field of allergy, and refers to insects belonging to the worldwide family of Vespidae, i.e., social wasps including hornets, yellowjackets, and paper wasps. In particular, vespids include the subfamilies Vespidae and Politician. More particularly, the vespids include the genera Vespa Linnaeus, Vespula Thomson, Dolichovespula Rohwer, and Polistes Latreille. Species in the genus Vespula include but are not limited to *V. germanica* (Fab.), *V. squamosa* (Drury), *V. maculifrons* (Buysson), *V. flavopilosa* (Jacobson), *V. vulgaris* (L.), and *V. pensylvanica* (Saussure). Species in the genus Polistes include but are not limited to *P. annularis* (Linnaeus), *P. exclamans* (Viereck), *P. metricus* (Say), *P. fuscatus* (Fabricius), and *P. apachus* (Saussure). Species in the genus Dolichovespula include but are not limited to *D. maculata* (L.) and *D. arenaria* (Fab.). Species in the genus Vespa include but are not limited to *V. crabro* (L.) and *V. orientalis* (Linnaeus).

As used herein, the term "phospholipase" refers to the class of enzymes that act on phospholipid substrates, e.g., to hydrolyze fatty acids. In a specific embodiment a phospholipase catalyzes rapid hydrolysis of the acyl group at position 1 of synthetic phosphatidylcholines, and a slow hydrolysis of the acyl group at position 2.

Thus, the vespid phospholipases of the invention can have both $A_1$ and B types of phospholipase activities. The phospholipases of the invention can have low level lipase activity as well.

As used herein, the term "hyaluronidase" refers to the class of enzymes that act on the disaccharide unit of D-glucuronic acid and N-acetyl-D-glucosamine. Such enzymes mediate the hydrolysis of polymers of repeating disaccharides comprising D-glucuronic acid and N-acetyl-D-glucosamine. One example of such polymer is hyaluronic acid. Hyaluronidase catalyzes the release of reducing groups of N-acetylglucosamine from hyaluronic acid.

As used herein, the term "immunomodulatory" refers to an ability to increase or decrease an antigen-specific immune response, either at the B cell or T cell level. Immunomodulatory activity can be detected e.g., in T cell proliferation assays, by measurement of antibody production, lymphokine production or T cell responsiveness. In particular, in addition to affects on T cell responses, the immunomodulatory polypeptides of the invention may bind to immunoglobulin (i.e., antibody) molecules on the surface of B cells, and affect B cell responses as well.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, infra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementarity, variables well known in the art.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that directs the host cell to transport the polypeptide to the cell surface or secrete the polypeptide into the media, and this signal peptide is usually selectively degraded by the cell upon exportation. Signal sequences can be found associated with a variety of proteins native to prokaryotes and eukaryotes.

In accordance with the present invention there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The present invention is based, in part, on the cloning and sequence determination of various vespid venom phospholipases and hyaluronidases. The cloning and sequence determination of these vespid venom enzymes is highly significant, since vespid venom allergic conditions are common, and in some sensitive individuals an allergic reaction can proceed to anaphylaxis, which is potentially fatal. It is therefore of great importance that the nucleotide and amino acid sequence information for the vespid venom allergens is known so that accurate diagnostic information about the nature of the allergic condition, especially specific allergen sensitivities, can be determined and effective therapeutic treatments of the underlying allergic condition can be effected.

For the sake of clarity, the present invention is described in detail in sections relating to isolation of genes encoding vespid venom enzymes, expression of a polypeptide comprising an immunomodulatory fragment of a vespid venom enzyme, or derivatives and analogs of the vespid venom enzyme, assays with the recombinant vespid venom enzyme, or fragments, derivatives or analogs thereof, and finally therapeutic and diagnostic uses of the vespid venom enzyme, or fragments, derivatives or analogs thereof. In particular, the invention relates to the vespid venom enzymes phospholipase and hyaluronidase.

Isolation of a Nucleic Acid Encoding a Vespid Venom Enzyme

The invention particularly relates to isolated nucleic acids encoding vespid venom enzymes. The invention further relates to a cell line stably containing a recombinant nucleic acid encoding a vespid venom enzyme, and capable of expressing such nucleic acid to produce the protein or an immunomodulatory fragment of a vespid venom enzyme.

Derivatives of a vespid venom enzyme, such as fragments and fusion proteins (see Infra), are additionally provided, as well as nucleic acids encoding the same.

In a preferred aspect, the present invention provides the complete nucleic acid sequence of a vespid venom enzyme. In particular, the present invention provides the nucleic acid sequence of a vespid phospholipase, in particular *Dolichovespula maculata* (white-face hornet) phospholipase (Dol m I) and *Vespula vulgaris* (yellowjacket) phospholipase (Ves v I), and hyaluronidase, in particular *D. maculata* hyaluronidase.

In a specific embodiment, to obtain a nucleic acid encoding a vespid venom enzyme, polymerase chain reaction (PCR) is combined with the rapid amplification of cDNA ends (RACE) technique described by Frohman et al. (1988, Proc. Nat. Acad. Sci. USA 85:8998–9002; see also Frohman, 1990, Amplifications: A Forum for PCR Users 5:11) to amplify a fragment encoding a sequence comprising the vespid venom enzyme prior to selection. Oligonucleotide primers representing a vespid venom enzyme of the invention can be used as primers in PCR. Generally, such primers are prepared synthetically. Sequences for such oligonucleotide primers can be deduced from amino acid sequence information. Such oligonucleotide sequences may be non-degenerate, but more frequently the sequences are degenerate. More preferably, the primers are based on the nucleic acid sequences for the vespid venom enzymes disclosed herein. The oligonucleotides may be utilized as primers to amplify by PCR sequences from a source (RNA or DNA), preferably a cDNA library, of potential interest. For example, PCR can be used to amplify a vespid venom enzyme coding sequence from a vespid acid gland cDNA library. PCR can be carried out, e.g., by use of a Perkin-Elmer Cetus thermal cycler and Taq polymerase (Gene Amp).

The present invention further provides for isolating a homolog of a vespid venom enzyme from any species of vespid. One can choose to synthesize several different degenerate primers for use, e.g., in PCR reactions. It is also possible to vary the stringency of hybridization conditions used in priming PCR reactions, to allow for greater or lesser degrees of nucleotide sequence similarity between a homolog of a vespid venom enzyme and a specific vespid venom enzyme disclosed herein. After successful amplification of a segment of a homolog of a vespid venom enzyme, that segment may be cloned and sequenced, and utilized as a probe to isolate a complete cDNA or genomic clone. This, in turn, will permit the determination of the complete nucleotide sequence, the analysis of its expression, and the production of its protein product for functional analysis, as described infra. In this fashion, additional genes encoding vespid venom enzymes, in particular, phospholipases and hyaluronidases, may be identified and expressed.

In another embodiment, genes encoding a vespid venom enzyme can be isolated from a suitable library by screening with a probe. Useful probes for isolating a vespid venom enzyme gene can be generated from the sequence information provided herein.

An expression library can be constructed by methods known in the art. Preferably, a cDNA library is prepared from cells or tissues that express a vespid venom enzyme, i.e., cells from the poison gland located near the venom sac.

Sometimes the poison gland is referred to as the acid gland. For example, mRNA or total RNA can be isolated, cDNA is made and ligated into an expression vector (e.g., a plasmid or bacteriophage derivative) such that it is capable of being expressed by the host cell into which it is then introduced. Various screening assays can then be used to select for the positive clones. For example, PCR with appropriate primers, which can be synthesized based on the sequences provided herein, can be used. PCR is preferred as the amplified production can be directly detected, e.g., by ethydium bromide staining. Alternatively, labelled probes derived from the nucleic acid sequences of the instant application can be used to screen the colonies.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for a vespid venom enzyme.

Some recombinant proteins expressed by bacteria, e.g., vespid venom hyaluronidases, are reactive with antibodies specific for the native proteins. Other bacterially expressed recombinant proteins, such as vespid phospholipases, do not react with antibodies specific for the native protein. Thus, in cases where the recombinant proteins are immunoreactive, it is possible to select for positive clones by immunoblot.

In another embodiment, the specific catalytic activity of the enzyme, such as lipase activity of an expressed vespid venom phospholipase, can be used for selection. However, bacterially expressed eukaryotic proteins may not fold in an active conformation.

Generally, according to the present invention, any method of screening for positive clones can be used.

Alternatives to isolating the vespid venom enzyme genomic DNA or cDNA include, but are not limited to, chemically synthesizing the gene sequence itself from the sequence provided herein.

The above methods are not meant to limit the methods by which clones of a vespid venom enzyme may be obtained.

A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as various pBR322 derivatives, for example, pUC, CR, pGEX vectors, pmal-c, pFLAG, etc. The insertion into a cloning vector can, for example, be accomplished by ligating the DNA fragment into a cloning vector which has complementary cohesive termini. In a preferred aspect of the invention, the PCR amplified nucleic acids of the invention contain 3'-overhanging A-nucleotides, and can be used directly for cloning into a pCR vector with compatible T-nucleotide overhangs (Invitrogen Corp., San Diego, Calif.). However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and a vespid venom enzyme gene may be modified by homopolymeric tailing. Recombinant molecules can be introduced into host cells via transformation, transfection, infection, electroporation, etc., so that many copies of the gene sequence are generated.

In specific embodiments, transformation of host cells with recombinant DNA molecules that incorporate the isolated vespid venom enzyme gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

Expression of a Vespid Venom Allergen Polypeptide or Fragment

The nucleotide sequence coding for a vespid venom enzyme, or an immunomodulatory fragment, derivative or analog thereof, can be inserted into an appropriate expression vector, i.e., a vector which contains the necessary elements for the transcription and translation of the inserted protein-coding sequence. Such elements are termed herein a "promoter." Thus, the nucleic acid encoding the vespid venom enzyme is operationally associated with the promoter. An expression vector also preferably includes a replication origin. The necessary transcriptional and translational signals can also be supplied by the native gene encoding a vespid venom enzyme and/or its flanking regions. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In an alternative embodiment, a recombinant vespid venom enzyme of the invention, or an immunomodulatory fragment, derivative or analog thereof, is expressed chromosomally, after integration of the vespid venom enzyme coding sequence by recombination. In this regard, any of a number of amplification systems may be used to achieve high levels of stable gene expression (See Sambrook et al., 1989, supra, at Section 16.28).

The cell into which the recombinant vector comprising the nucleic acid encoding the vespid venom enzyme is cultured in an appropriate cell culture medium under conditions that provide for expression of the vespid venom enzyme by the cell. The expressed vespid venom enzyme can then be recovered from the culture according to methods well known in the art. Such methods are described in detail, infra.

In a another embodiment, a vespid venom enzyme-fusion protein can be expressed. A vespid venom enzyme-fusion protein comprises at least a functionally active portion of a non-vespid venom enzyme protein joined via a peptide bond to at least an immunomodulatory portion of a vespid venom enzyme. The non-vespid venom enzyme sequences can be amino- or carboxyl-terminal to the vespid venom enzyme sequences. A recombinant DNA molecule encoding such a fusion protein comprises a sequence encoding at least a functionally active portion of a non-vespid venom enzyme joined in-frame to the coding sequence for a vespid venom enzyme, and preferably encodes a cleavage site for a specific protease, e.g., Factor Xa, preferably at the juncture of the two proteins.

In another specific embodiment, a fragment of the vespid venom enzyme is expressed as a free (non-fusion) protein.

In a specific embodiment, the vespid venom phospholipase, and immunomodulatory fragments thereof, are expressed with an additional sequence comprising about six histidine residues, e.g., using the pQE12 vector (QIAGEN, Chatsworth, Calif.). The presence of the histidine makes possible the selective isolation of recombinant proteins on a Ni-chelation column.

In another embodiment, a periplasmic form of the fusion protein (containing a signal sequence) can be produced for export of the protein to the *Escherichia coli* periplasm. Export to the periplasm can promote proper folding of the expressed protein.

Any of the methods previously described for the insertion of DNA fragments into a vector may be used to construct expression vectors containing a gene consisting of appropriate transcriptional/translational control signals and the protein coding sequences. These methods may include in vitro recombinant DNA and synthetic techniques and in vivo recombinants (genetic recombination). Expression of nucleic acid sequence encoding a vespid venom enzyme, or an immunomodulatory fragment thereof, may be regulated by a second nucleic acid sequence so that the vespid venom enzyme protein or peptide is expressed in a host transformed with the recombinant DNA molecule. For example, expression of a vespid venom enzyme protein may be controlled by any promoter/enhancer element known in the art, but these regulatory elements must be functional in the host selected for expression. Promoters which may be used to control vespid venom enzyme gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Expression vectors containing a nucleic acid encoding a vespid venom enzyme can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted vespid venom enzyme gene. In the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In a specific example, the fusion protein comprises the "marker" gene product and a vespid venom enzyme. In another example, if the nucleic acid encoding a vespid venom enzyme is inserted within the marker gene sequence of the vector, recombinants containing the vespid venom enzyme insert can be identified by the absence of the marker gene function. In the fourth approach, recombinant expression vectors can be identified by assaying for the activity of the gene product expressed by the recombinant, provided that the expressed protein folds into the appropriate conformation. Such assays can be based, for example, on the physical or functional properties of the a vespid venom enzyme gene product in in vitro assay systems, e.g., phospholipase or lipase activity of vespid venom phospholipases, or hyaluronidase activity of vespid venom hyaluronidases, or alternatively binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the enzyme protein expressed in bacteria may not be properly folded. Expression in yeast can produce a glycosylated product. Expression in insect cells can be used to increase the likelihood of "native" glycosylation and folding of a heterologous vespid venom enzyme. Furthermore, different vector/host expression systems may affect processing reactions, such as proteolytic cleavages, to a different extent. It is interesting to note that it has been observed that glycosylation and proper refolding are not essential for immunomodulatory activity of a vespid venom allergen since bacterial-produced allergen is active in a T cell proliferation assay.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Both cDNA and genomic sequences can be cloned and expressed.

It is further contemplated that the vespid venom enzymes of the present invention, or fragments, derivatives or analogs thereof, can be prepared synthetically, e.g., by solid phase peptide synthesis.

Once the recombinant vespid venom enzyme protein is identified, it may be isolated and purified by standard methods including chromatography (e.g., ion exchange, affinity, and sizing column chromatography), centrifugation, differential solubility, or by any other standard technique for the purification of proteins.

In a specific embodiment, a vespid venom enzyme and fragments thereof can be engineered to include about six histidyl residues, which makes possible the selective isolation of the recombinant protein on a Ni-chelation column. In a preferred aspect, the proteins are further purified by reverse phase chromatography.

In another embodiment, in which recombinant vespid venom enzyme is expressed as a fusion protein, the non-vespid venom enzyme portion of the fusion protein can be targeted for affinity purification. For example, antibody specific for the non-vespid venom enzyme portion of the fusion protein can be immobilized on a solid support, e.g., cyanogen bromide-activated Sepharose, and used to purify the fusion protein. In another embodiment, a binding partner of the non-vespid venom enzyme portion of the fusion protein, such as a receptor or ligand, can be immobilized and used to affinity purify the fusion protein.

In one embodiment, a vespid venom enzyme-fusion protein, preferably purified, is used without further modification, i.e., without cleaving or otherwise removing the non-vespid venom enzyme-portion of the fusion protein. In a preferred embodiment, the vespid venom enzyme-fusion protein can be used therapeutically, e.g., to modulate an immune response.

In a further embodiment, the purified fusion protein is treated to cleave the non-vespid venom enzyme protein or portion thereof from the vespid venom enzyme. For example, where the fusion protein has been prepared to include a protease sensitive cleavage site, the fusion protein can be treated with the protease to cleave the protease specific site and release vespid venom enzyme. In a specific embodiment, the fusion protein is cleaved by treatment with Factor Xa.

In a further embodiment, the vespid venom phospholipase protein can be refolded.

In a specific embodiment of the present invention, such recombinant vespid venom enzymes include but are not limited to those containing, as a primary amino acid sequence, all or part of the amino acid sequence substantially as depicted in FIGS. 1 (SEQ ID NO:17), 5 (SEQ ID NO:27), or 6 (SEQ ID NO:55), as well as fragments and other derivatives, and analogs thereof.

Derivatives and Analogs of Vespid Venom Enzymes

The invention further relates to derivatives and analogs of vespid venom enzymes. The production and use of derivatives and analogs related to vespid venom enzymes are within the scope of the present invention. The derivative or analog is immunomodulatory, i.e., capable of modulating an antigen-specific immune response. In another embodiment, the derivative or analog can bind to a vespid venom enzyme-specific immunoglobulin, including IgG and IgE. Derivatives or analogs of vespid venom enzyme can be tested for the desired immunomodulatory activity by procedures known in the art, including but not limited to the assays described infra.

In particular, vespid venom enzyme derivatives can be made by altering the nucleic acid sequences of the invention by substitutions, additions or deletions that provide for functionally equivalent molecules. Due to the degeneracy of nucleotide coding sequences, other DNA sequences which encode substantially the same amino acid sequence as a nucleic acid encoding a vespid venom enzyme may be used in the practice of the present invention. These include but are not limited to nucleotide sequences comprising all or portions of a gene encoding the vespid venom enzyme that are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of a vespid venom enzyme, including altered sequences in which functionally equivalent amino acid residues are substituted for residues within the sequence resulting in a conservative amino acid substitution. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of vespid venom enzyme include but are not limited to those which are substantially homologous to a vespid venom enzyme or fragments thereof, or whose encoding nucleic acid is capable of hybridizing to a nucleic acid encoding a vespid venom enzyme. Hybridization can occur under moderately stringent to highly stringent conditions, depending on the degree of sequence similarity, as is well known in the art.

The derivatives and analogs of the invention can be produced by various methods known in the art. The manipulations which result in their production can occur at the gene or protein level. For example, the nucleic acid sequence of the cloned vespid venom enzyme can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of a vespid venom enzyme, care should be taken to ensure that the modified gene remains within the same translational reading frame as vespid venom enzyme, uninterrupted by translational stop signals.

Additionally, the gene encoding a vespid venom enzyme can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Manipulations of the recombinant vespid venom enzyme may also be made at the protein level. Included within the scope of the invention are recombinant vespid venom enzyme fragments or other derivatives or analogs which are differentially modified during or after translation, e.g., by glycosylation, acetylation, phosphorylation, amidation, reduction and carboxymethylation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NABH_4$; acetylation, formylation, oxidation, reduction; metabolic synthesis in the presence of tunicamycin; etc.

In a particular embodiment, the vespid venom enzyme or immunomodulatory fragment thereof is expressed in an insect cell expression system, e.g., using a baculovirus expression vector. As pointed out above, this should yield "native" glycosylation and structure, particularly secondary and tertiary structure, of the expressed polypeptide. Native glycosylation and structure of the expressed polypeptide may be very important for diagnostic uses, since the enzyme specific antibodies detected in diagnostic assays will be specific for the native enzyme, i.e., as introduced by a sting from a vespid.

Activity Assays With Peptides of the Invention

Numerous assays are known in immunology for evaluating the immunomodulatory activity of an antigen. For example, the vespid venom enzyme proteins produced by expression of the nucleic acids of the invention can be used in diagnostic assays for allergic diseases, which are described in detail, infra. In general, such proteins can be tested for the ability to bind to antibodies specific for the enzyme. Preferably, such antibodies that are detected in the diagnostic assay are of the IgE class. However, it is important to note that natural allergen-specific antibodies have been found to bind weakly to denatured vespid venom allergens. Vespid venom enzymes produced in eukaryotic expression systems, and particularly insect cell expression systems, may have the correct structure for antibody binding. Vespid venom enzymes expressed in bacterial expression systems may not, and would thus require refolding prior to use in a diagnostic assay for antibody binding.

In another embodiment, the proteins of the invention can be tested in a proliferation assay for T cell responses. For such T cell response assays, the expression system used to produce the enzyme does not appear to affect the immunomodulatory activity of the protein. Generally, lymphocytes from a sensitized host are obtained. The host can be a mouse that has been immunized with a vespid venom enzyme, such as a vespid venom phospholipase or hyaluronidase that has been produced recombinantly according to the present invention.

In a preferred embodiment, peripheral blood leukocytes are obtained from a human who is sensitive to vespid venom. Using techniques that are well known in the art, T lymphocyte response to the protein can be measured in vitro. In a specific embodiment, infra, T cell responses are detected by measuring incorporation of $^3$H-thymidine, which increases with DNA synthesis associated with proliferation.

Cell proliferation can also be detected using an MTT assay (Mossman, 1983, J. Immunol. Methods 65:55–63; Niks and Otto, 1990, J. Immunol. Methods 130:140–151). Any method for detecting T cell proliferation known in the art can be used with the vespid enzyme produced according to the present invention.

Similarly, lymphokine production assays can be practiced according to the present invention. In one embodiment, lymphokine production can be assayed using immunological or co-stimulation assays (see, e.g., Fehlner et al., 1991, J. Immunol. 146:799) or using the ELISPOT technique (Czerkinsky, et al., 1988, J. Immunol. Methods 110:29). Alternatively, mRNA for lymphokines can be detected, e.g., by amplification (see Brenner, et al., 1989, Biotechniques 7:1096) or in situ hybridization (see, e.g., Kasaian and Biron, 1989, J. Immunol. 142:1287). Of particular interest are those individuals whose T cells produce lymphokines associated with IgE isotype switch events, e.g., IL-4 and IL-5 (Purkeson and Isakson, 1992, J. Exp. Med. 175:973–982). Also of interest are the polypeptide fragments of the vespid venom enzyme that contain epitopes recognized by T cells involved in IgE switch events.

Thus, in a preferred aspect, the proteins produced according to the present invention can be used in in vitro assays with peripheral blood lymphocytes or, more preferably, cell lines derived from peripheral blood lymphocytes, obtained from vespid venom enzyme sensitive individuals to detect secretion of lymphokines ordinarily associated with allergic responses, e.g., IL-4. Such assays may indicate which venom component or components are responsible for the allergic condition. More importantly, the fragments of the vespid venom enzyme can be tested. In this way, specific epitopes responsible for T cell responses associated with allergic response can be identified. The sequences of such epitopes can be compared to other vespid venom enzymes and to environmental or autologous proteins to determine if there are sequence similarities that suggest possible cross-reactivity. The peptides can be tested for the ability to induce T cell anergy, e.g., by mega-dose administration, modification to produce an epitope antagonist, administration in the absence of the appropriate costimulatory signals, and other methods thought to result in T cell anergy. Peptides containing such epitopes are ideal candidates for therapeutics.

In a further embodiment, the polypeptides of the invention can be used directly in assays to detect the extent of cross-reactivity with other environmental proteins and/or homologous proteins, with which they share sequence similarity. In particular, the fragments of the vespid venom enzymes that have sequence similarity with such environmental, and more particularly, homologous proteins can be evaluated for cross reactivity with antibodies or T cell specific for such proteins. In a specific embodiment, the cross reactivity of vespid venom phospholipases with human lipases can be evaluated. In another specific embodiment, the cross reactivity of vespid venom hyaluronidase with the sperm membrane protein PH-20 is evaluated.

Diagnostic and Therapeutic Uses of the Vespid Venom Enzyme Polypeptides

The present invention provides a plentiful source of a pure vespid venom enzyme, or fragments, derivatives or analogs thereof, produced by recombinant techniques. Alternatively, given the sequence information provided by the present invention, polypeptide fragments, derivatives or analogs of the vespid venom enzymes can advantageously be produced by peptide synthesis.

The invention contemplates use of vespid venom enzymes, or immunomodulatory fragments, derivatives or analogs thereof for the preparation of diagnostic or therapeutic compositions, for the use in the diagnosis and therapy of vespid venom allergen-specific allergic conditions. In particular, vespid phospholipase, more particularly *Dolichovespula maculata* (white-face hornet) phospholipase (Dol m I) and *Vespula vulgaris* (yellowjacket) phospholipase (Ves v I), or vespid hyaluronidase, in particular *D. maculata* hyaluronidase, or immunomodulatory fragments, derivatives or analogs of phospholipase or hyaluronidase, are contemplated for use in diagnosis and therapy according to the present invention.

Diagnostic Methods

As use herein, the term diagnostic includes in vitro and in vivo diagnostic assays. Generally, such assays are designed to measure the activity of IgE antibodies specific for a given allergen. Such diagnostic assays depend heavily on the availability of pure allergen. This is especially true for determining sensitivity to a specific allergen component of a vespid venom. In vitro diagnostic assays for enzyme sensitivity include radioimmunoassay (RIA), immunoradiometric immunoassay (IRMA), radio-allergosorbent tests (RAST), enzyme-linked immunosorbent assay (ELISA), ELISPOT, magnetic allergosorbent assay, immunoblots, histamine release assays, and the like.

In a further embodiment, the present invention provides for determining the presence of epitopes that are predominantly reactive with IgE antibodies, or with other isotypes, e.g., IgG. Such epitopes may overlap or be distinct. In particular, fragments of the vespid venom enzymes of the invention can be used to identify such specific B cell epitopes. Identification of specific epitopes can provide a basis for developing therapies, as described infra.

The present invention contemplates in vitro diagnostic assays on peripheral blood lymphocytes, as described supra. Such diagnostic assays can give detailed information about the enzyme-specific T cell responses, the phenotype of the T cell response, and preferably the T cell epitope of the enzyme involved in T cell responses. The immunodominant epitope and the epitope involved in IgE isotype class switch events can be detected, if they are not the same. In particular, the T cell epitopes of vespid venom enzymes that stimulate proliferation and/or lymphokine secretion of T cells of a phenotype associated with IgE isotype class switching events can be identified for a specific individual, or for a class of individuals who share MHC haplotype or a predominant T cell receptor variable region expression, or both.

In vivo assays for allergenicity generally consist of skin prick sensitivity assays, in which serially diluted amounts of an allergen are administered either subcutaneously or intradermally into a patient's skin, and wheel and erythema reactions are detected. As with in vitro assays, the availability of pure venom enzyme greatly increases the value of the results of the in vivo diagnostic assays since cross-reactivity with impurities in extracts prepared from vespid venom sacs can be avoided.

Therapeutic Methods

Therapeutic compositions of the invention (see, infra) can be used in immunotherapy, also referred to as hyposensitization therapy. Immunotherapy has proven effective in allergic diseases, particular insect allergy. Allergens are administered parenterally over a long period of time in gradually increasing doses. Such therapy may be particularly effective when the allergen or allergens to which the patient is sensitive have been specifically identified and the therapy is targeted to those allergen(s). Thus, the availability of pure vespid venom enzyme in large quantities is important for immunotherapy of allergy.

In another embodiment, the present invention contemplates use of polypeptides containing at least an immunomodulatory T cell epitope of a vespid venom enzyme to induce specific T cell anergy to the vespid venom enzyme. Identification of such peptides is described supra. More preferably, a peptide comprising such a T cell epitope and lacking a B cell epitope can be administered to a patient.

As discussed in the Background of the Invention, the presence of B cell epitopes on an allergen can cause an undesirable systemic reaction when the allergen is used for immunotherapy. Thus, a particular advantage of the invention is the capability to provide allergen polypeptides that do not cause undesirable systemic effects.

In one embodiment, one or more polypeptide fragments can be injected subcutaneously to decrease the T cell response to the entire molecule, e.g., as described by Brine et al. (1993, Proc. Natl. Acad. Sci. U.S.A. 90:7608–12).

In another embodiment, one or more polypeptide fragments can be administered intranasally to suppress allergen-specific responses in naive and sensitized subjects (see e.g., Hoyne et al., 1993, J. Exp. Med. 178:1783–88).

Administration of a vespid venom enzyme peptide of the invention is expected to induce anergy, resulting in cessation of allergen-specific antibody production or allergen-specific T cell response, or both, and thus, have a therapeutic effect.

In a preferred aspect of the invention, peptide based therapy to induce T cell anergy is customized for each individual or a group of individuals. Using the diagnostic methods of the present invention, the specific T cell epitope or epitopes of a vespid venom enzyme involved in the allergic response can be identified. Peptides comprising these epitopes can then be used in an individualized immunotherapy regimen.

Pharmaceutically Acceptable Compositions

The in vivo diagnostic or therapeutic compositions of the invention may also contain appropriate pharmaceutically acceptable carriers, excipients, diluents and adjuvants. As used herein, the term "pharmaceutically acceptable" preferably means approved by a regulatory agency of a government, in particular the Federal government or a state government, or listed in the U.S. Pharmacopeia or another generally recognized pharmacopeia for use in animals, and more particularly in humans. Suitable pharmaceutical carriers are described in "Remington's Pharmaceutical Sciences" by E. W. Martin.

Such pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include mannitol, human serum albumin (HSA), starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

Such compositions will contain an effective diagnostic or therapeutic amount of the active compound together with a suitable amount of carrier so as to provide the form for proper administration to the patient. While intravenous injection is a very effective form of administration, other modes can be employed, such as by injection, or by oral, nasal or parenteral administration.

The invention will be further clarified by the following examples, which are intended to be purely exemplary of the invention.

EXAMPLE 1

Hornet Venom Phospholipase

In a continuing effort to understand what immunochemical properties of a protein contribute to its allergenicity, the second major allergen of hornet venom was cloned and sequenced. According to an accepted allergen nomenclature system (Marsh, et al., 1987, J. Allergy Clin. Immunol. 80:639), white-faced hornet phospholipase is designated Dol m I.

In particular, the sequence of a venom allergen phospholipase from white-faced hornet (*Dolichovespula maculata*) has been determined by cDNA and protein sequencings. This protein of 300 amino acid residues (Dol m I) has no sequence similarity with other known phospholipases. However, it has sequence similarity with mammalian lipases; about 40% identity in overlaps of 123 residues. Natural hornet phospholipase was also found to have weak lipase activity.

Materials and Methods

Isolation and characterization of Dol m I and its CNBr peptides. Dol m I was isolated from venom sac extracts of white-faced hornet (Vespa Laboratory, Spring Mills, Pa.) as described (King, et al., 1985, J. Allergy and Clin. Immunol. 75:621). The protein (0.6 mg) was cleaved with CNBr (15 mg) in 75% $HCO_2H$ (0.2 ml) at 25° overnight. After cleavage the lyophilized mixture was separated on a Pep-RPC column (Pharmacia, Piscataway, N.J.) with a 2-propanol gradient of 0.1% per ml in 0.1% trifluoroacetic acid at a flow rate of 40 ml per hour. Selected fractions were rechromatographed under the same conditions after reduction and S-carboxymethylation (Fang, et al., 1988, Proc. Natl. Acad. Sci., USA. 85:895). The recovered peptides were characterized by Edman degradation on an Applied Biosystems gas phase sequencer.

Dol m I-specific cDNA. Total RNAs were isolated from the acid gland of white-faced hornet using the guanidine thiocyanate extraction procedure (Fang, et al., 1988, supra). Dol m I-specific cDNA was obtained from total RNAs by the procedure of Frohman (Frohman, 1990, Amplifications: A Forum for PCR Users, 5:11; Frohman, et al., 1988, Proc. Natl. Acad. Sci. USA. 85:8998–9002) for rapid amplification of 3' or 5' cDNA ends (RACE).

First strand cDNAs were prepared using MeHgOH (Invitrogen, San Diego, Calif.) denatured total RNAs ($6\mu$) as the template and other reagents of a cDNA synthesis kit from GMCO-BRL (Gaithersburg, Md.) and RNasin (Promega Biotech) in a total reaction volume of 37 $\mu$l. For 5' RACE, the single strand cDNAs (from 6 $\mu$g of total RNAs) were poly-dA tailed with terminal deoxynucleotidyl transferase (US Biochemical, Cleveland, Ohio). The 3' or 5' RACE was carried out a with GenAmp PCR reagent kit (Perkin-Elmer Cetus, Norwalk, Conn.) using AmpliTaq polymerase, and 3' RACE was also made with Vent polymerase (New England Biolabs, Beverly, Mass.). For first round PCR, $\frac{1}{100}$ of the first strand cDNAs were used as a template. For the second round PCR, $\frac{1}{1000}$ of the first round PCR products were used as a template.

PCR products were examined by electrophoresis in 1.5% agarose gel with ethidium bromide staining and by Southern blot analysis. DNA was transferred to nitrocellulose membrane (Schleicher & Schuell, Keene, N.H.) and then was immobilized by UV cross-linking. Membranes were soaked for 2 hrs at 42° C. in a prehybridization solution of 30% formamide, 6× SSPE (Sambrook, et al., 1989, Molecular Cloning. Vol. 1 and 2, Cold Spring Harbor Laboratory Press), 5× Denhardt's solution (Sambrook, et al., 1989, supra), 100 $\mu$g/ml salmon sperm DNA, 0.1% SDS, and then hybridized overnight at 42° C. with $^{32}$P-labeled oligonucleotide probe ($1\times10^6$ cpm per ml of prehybridization solution). Post hybridization membranes were twice washed for 20 min at 60° in a solution of 3 M tetramethylammonium chloride, 0.2% SDS and 0.05 M Tris-HCl, pH 8.0 (Wood, et al., 1985, Proc. Natl. Acad. Sci. USA. 82:1585–1588). Oligonucleotides of specific activity $5\times10^7$ to $10^8$ cpm/$\mu$g were labeled with $\gamma$-$^{32}$P-ATP (New England Nuclear Corp) in presence of T4 polynucleotide kinase (New England Biolabs). The labeling procedure as well as other molecular biology procedures were taken from Sambrook, et al. (1989, supra).

PCR products contain single 3'-overhanging A-nucleotides (Clark, 1988, Nucl. Acids Res. 16:9677–9686) and were used directly for cloning into the PCR vector with compatible T-nucleotide overhangs (Invitrogen Corp, San Diego, Calif.). Plasmid DNAs were isolated from appropriate clones using the QIAGEN plasmid kit (QIAGEN, Chatsworth, Calif.).

DNA sequences were determined by the dideoxynucleotide chain-termination method (Sanger, et al., 1977, Proc. Natl. Acad. Sci. 74:5463–5467) using alkaline denatured plasmid DNAs and the Sequenase version 2.0 kit (US Biochemical, Cleveland, Ohio).

Cloning and attempted expression of phospholipase. cDNA encoding the complete sequence of phospholipase, residues 1–300, was obtained by PCR using primers derived from the composite sequence. The primers were synthesized with overchanging BamHI and BglII restriction sites. The PCR product was digested with BamHI and BglII, and ligated with similarly cut pQE-12 plasmid with complementary cohesive ends (QIAGEN, Chatsworth, Calif.). The recombinant pQE-12 plasmid was used to transform competent M15 (pREP) bacteria.

The pCR product without BamHI and BglII digestions was also cloned directly into the pCR vector (Invitrogen). The recombinant pCR vector was used to transform INVαF' bacteria.

Phospholipase and lipase assays. Phospholipase activity was measured titrimettically at 25±1° and pH 8 with 10% egg yolk as substrate in 0.2 N NaCl containing 0.5% Triton (King, et al., 1984, Arch. Biochem. Biophys. 230:1). Lipase activity was measured similarly using emulsions of 2% synthetic triglycerides triacetin, tributyrin, tricaprylin, triolein or tristearin (Sigma Biochemical, St. Louis, Mo.) as substrates.

Results

Partial amino acid sequence of Dol m I. Partial amino acid sequence data were obtained from CNBr peptides. The partial or complete sequences of seven of these peptides correspond to residue 1–12, 14–30, 32–57, 85–96, 98–112, 161–170, 183–194 and 244–251 of the molecule which are shown with underlines in FIG. 1. The first five peptides correspond to the expected cleavage as in each case either preceded or terminated with a methionine residue. The last three peptides represent side products from acid cleavage of glutamyl peptide bonds. These partial amino acid sequence data were used for the design and synthesis of oligonucleotides SEQ ID NOS. 5, 6, 9 and 11 in Table 1.

fying the cDNA region which is 5' of nucleotide 115 in FIG. 1. As shown schematically in FIG. 2B, single stranded Dol

TABLE 1

Oligonucleotides used as primers or probes for cloning hornet phospholipase

| SEQ. ID. No. | Oligonucleotide* | Comment |
|---|---|---|
| 1 | AAG GAT CCG TCG ACA TCG ATA ATA CGA CTC ACT ATA GGG ATT $T_{15}$ | $(dT)_{17}$ $R_1R_0$ primer for first strand cDNA synthesis of 3' RACE. |
| 2 | AAG GAT CCG TCG ACA TC | $R_0$ anti-sense primer for first round PCR of 3' RACE. |
| 3 | GAC ATC GAT AAT ACG AC | $R_1$ anti-sense primer for second round PCR of 3' RACE. |
| 4 5 | $D^9$ T V K M $I^{14}$<br>GAY ACI GTI AAR ATG AT | Sense primer for first round PCR of 3' RACE. |
| 6 7 | $7K^{22}$ H D F Y $T^{27}$<br>AAR CAY GAY TTY TAY AC | Sense primer for second round PCR of 3' RACE. |
| 8 9 | $I^{190}$ Q V Y H A $D^{184}$<br>AT YTG IAC RTA RTG IGC RTC | Hybridization probe of PCR produce of 3' RACE; or primer for first strand cDNA synthesis of 5' RACE. |
| 10 11 | $P^{92}$ Y E D T $C^{87}$<br>GG RTA YTC RTC IGT RCA | Anti-sense primer for first round PCR of 5' RACE. |
| 12 13 | $M^{70}$ L A E $S^{66}$<br>G CAT AAG AGC CTC TGA C | Anti-sense primer for second round PCR of 5' RACE. |
| 14 15 | $M^{31}$ T D L $T^{27}$<br>T CAT TGT ATC TAG CGT A | Hybridization probe for PCR product of 5' RACE. |

Figure 3:
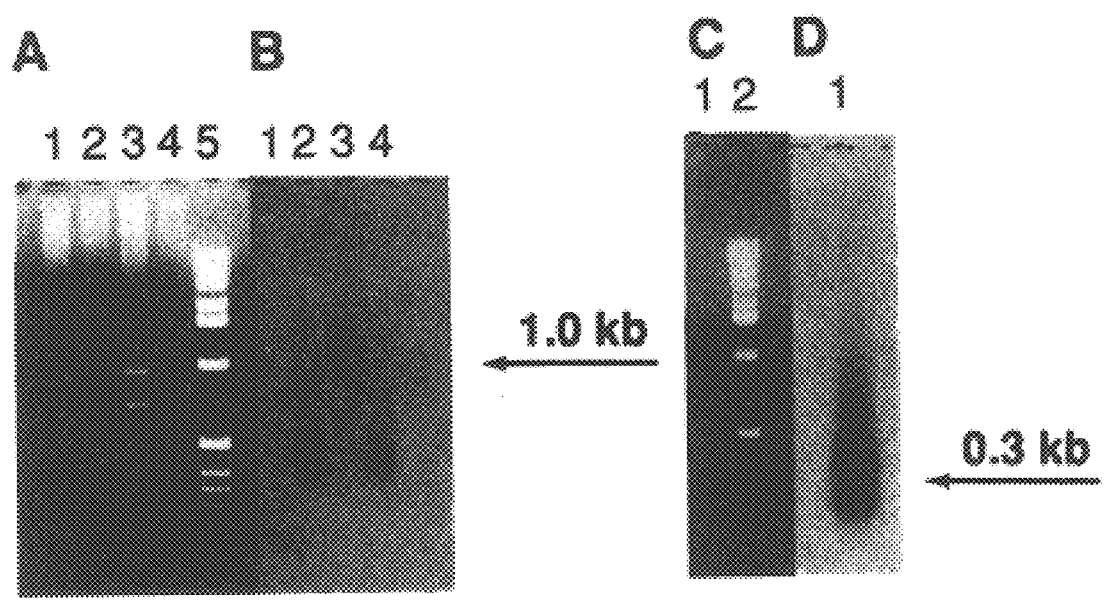
FIG. 3. 3' and 5' RACE of white-faced hornet phospholipase-specific cDNA. In panels A and B are shown respectively the agarose gel electrophoresis and Southern blot analysis products for 3' RACE. In lanes 1 and 3 are shown the products from first and second rounds of PCR obtained with AmpliTaq DNA polymerase, in lanes 2 and 4 are shown similar products obtained with Vent polymerase; and in lane 5 is shown a 1 kb DNA Ladder (BRL). In panels C and D are shown similar results (as in panels A and B) for 5' RACE products (lane 1) obtained with AmpliTaq DNA polymerase; and in lane 2 (panel C) is shown the 1 kb DNA Ladder. The arrows in panels B and D indicate the desired products. The hybridization probes are given in Table 1.

*R represents A or G; Y represents C or T; I represents inosine.

cDNA sequence of Dol m I. cDNA encoding amino acid residues 22 to 300 and its 3'-untranslated region was amplified from venom RNAs by the RACE procedure as outlined in FIG. 2A. Single stranded venom cDNAs were synthesized from total RNAs using a dT primer with $R_t+R_o$ adapter (oligonucleotide SEQ ID NO:1 in Table 1). Double stranded Dol m I-specific cDNA was amplified from single stranded venom cDNAs by two successive rounds of PCR using the nested primers as indicated. Several PCR products were detected and a major band of about 1 kb (FIG. 3) appeared to be the expected product when tested on Southern blot by hybridization with oligonucleotide SEQ ID NO:9 (Table 1). As shown in FIG. 3, the 1 kb band was only found when Taq polymerase was used and it was not found with Vent polymerase.

The PCR products which contain the 1 kb band were cloned directly into plasmids. After transformation into bacteria, plasmids from 3 colonies were selected and sequenced. The composite sequences of two colonies gave the nucleotide sequence of 115 to 1050 in FIG. 1 (SEQ ID NO:16). One of them differs from that shown by the deletion of one adenine base at position 968, and by the insertion of an additional 99 nucleotides at position 1027 in the 3'-untranslated region. A third colony differs from that shown at position 807 (C to T substitution; both encoding serine) and at position 812 (A to G substitution; asparagine to serine change).

Using the cDNA data of FIG. 1, oligonucleotides of SEQ ID NOS. 13 and 15 in Table 1 were synthesized for amplim I-specific cDNA was synthesized from total RNAs using oligonucleotide SEQ ID NO:9 as the primer, then poly-dA tailed with terminal deoxynucleotidyl transferase. Double-stranded Dol m I-specific cDNA was amplified from poly-dA tailed specific cDNA by two successive rounds of PCR with the indicated primers. Several products formed after the second round of amplification and two bands of about 0.32 and 0.25 kbp (FIG. 3) appeared to be the expected products when detected on Southern blot by hybridization with oligonucleotide SEQ ID NO:15 in Table 1. Following cloning into a plasmid, the product of 0.32 kbp was established to contain the cDNA sequence from nucleotide 1 to 262 in FIG. 1.

The region preceding nucleotide position 52 in FIG. 1 encodes a leader sequence of 17 amino acid residues as the N-terminal amino acid residue of Dol m I. The Dol m I protein was found on Edman degradation to begin at nucleotide position 52. The protein sequence suggests the presence of two possible glycosylation sites at residue 8 and 212. The site at residue 8 is probably glycosylated as repeated attempts to identify this residue by Edman degradation gave negative results. The presence of a carbohydrate on the Dol m I protein is also suggested by the difference in the molecular weight of 33,745, calculated from the deduced sequence, and the observed molecular weight of about 37,000, estimated from SDS gel electrophoresis.

cDNA encoding the complete sequence of phospholipase, residue 1–300, was obtained by PCR of venom cDNAs with the following two primers:

| primer | sequence | | | | | | | |
|---|---|---|---|---|---|---|---|---|
| sense | CGT | BamHI GGA TCC | F¹ TTC | S TCC | V GTA | C TGT | P CCC | F⁶ TTT | (SEQ ID NO:59) (SEQ ID NO:60) |
| anti-sense | CGT | BglII AGA TCT | I³⁰⁰ AAT | I TAT | K TTT | G CCC | N GTT | N²⁹⁵ GTT | (SEQ ID NO:61) (SEQ ID NO:62) |

The PCR product after BamHI and BglII digestions was ligated with similarly cut pQE-12 plasmid with complementary cohesive ends (QIAGEN, Chatsworth, Calif.). The recombinant pQE-12 plasmid was used to transform competent M15(pREP) bacteria. However, no expression of the desired recombinant protein was detected.

The above PCR product, without BamHI and BglII digestions, was also cloned directly into a pCR vector (Invitrogen, San Diego, Calif.). After transformation of INVαF' bacteria, the resulting plasmid was found to contain a cDNA insert having identical sequence with that shown in FIG. 1 for hornet phospholipase, with the exception that one nucleotide deoxythymidylate at position 322, had been deleted.

The pQE-12 system has been used successfully for the expression of hornet venom antigen 5 and hornet venom hyaluronidase (see Example 5). If the recombinant phospholipase is toxic to the bacterial host, the host may delete a nucleotide of the cDNA so that its reading frame is altered. This may be a possible explanation for the lack of expression of phospholipase. Alternatively, the PCR amplification may have introduced this deletion mutation, although this is unlikely.

A bacteria culture harboring the recombinant pCR plasmid, designated as WFH-PLA-E4, was deposited on Mar. 11, 1993 with American Type Culture Collection and assigned accession number ATCC 69254. Subsequent to making that deposit, repeated sequence analysis of this plasmid DNA showed that the mutations described above, deletion of the nucleotide deoxythymidylate at position 322 of the sequence given in FIG. 1, was present in this clone. Lipase activity of natural hornet phospholipase. It has been reported previously (King et al., 1985, J. Allergy Clin. Immunol. 75:621–628) that vespid phospholipase catalyzes a rapid hydrolysis of the acyl group at position 1 of synthetic phosphatidylcholines and slow hydrolysis of the acyl group at position 2. Therefore, vespid phospholipases have both $A_1$ and B types of phospholipase activities. The present finding on sequence similarity of hornet phospholipase with lipases prompted tests for lipase activity.

The batch of enzyme sample isolated from venom had about 280 units of phospholipase activity per mg when tested with egg yolk as a substrate. This is lower than the previously reported specific activity of 1,100 units per mg (King, et al., 1985, supra), and its low specific activity was due to inadvertent prolonged exposure to low pH. This sample had lipase activities of 13 and 33 (±20%) units/mg with triacetin and tributyrin, respectively, as substrates. These data indicate that hornet phospholipase has a weak lipase activity.

Discussion

Sequence comparison by the FASTA method (Pearson and Lipman, 1988, Proc. Natl. Acad. Sci. USA 85:2444) showed that Dol m I has no similarity with other known phospholipases in the literature, but it has similarity with mammalian lipases. This is shown in FIG. 4 for lipoprotein lipases and hepatic lipases from human and mouse (Kirchgessner, et al., 1987, J. Biol. Chem. 262:8463; Oka, et al., 1991, Biochim. Biophys. Acta. 1089:13). Human pancreatic lipase (Winkler, et al., 1990, Nature. 343:771) has about the same degree of similarity with Dol m I as human hepatic lipase. There is about 40% identity in overlaps of 123 residues of mammalian lipases and Dol m I. The sequence region of lipases shown in FIG. 4 is highly conserved as similar sequences are found for a number of other mammalian and prokaryotic lipases and a Drosophila protein vitellogenin (Persson, et al., 1989, Eur. J. Biochem. 179:39; Bownes, et al., 1988, Proc. Natl. Acad. Sci. USA. 85:1554). Thus these proteins also have significant sequence similarity with Dol m I.

The most strongly conserved region of all lipases is reported to be in the undecapeptide region of residue 153–163 of human lipoprotein lipase (Persson, et al., 1989, supra). This region is believed to be of importance for lipase activity, and it is the region of highest identity of lipases and Dol m I. Interestingly Dol m I does have weak lipase activity with synthetic triglycerides.

All vespid allergic patients invariably have antibodies specific for both Dol m I and V. Therefore we compared the sequences of these two proteins and they are found to share one similar octapeptide sequence: VNRHNQFR (SEQ ID NO:23) and LKRHDNDFR (SEQ ID NO:24) at position 45–52 of Dol m VA and B respectively, and MNRHNEFK (SEQ ID NO:25) at position 31–38 of Dol m I. However, this octapeptide sequence is not in the sequence region where these phospholipase show similarity with other proteins.

There are several examples of sequence similarity of allergens with other proteins in our environment. Some examples are: birch pollen allergen Bet v I with a pea disease resistance response gene (Breiteneder, et al., 1989, EMBO J. 8:1935); Bet v II and its homologs from timothy and mugwort pollens with human profilin (Valenta, et al., 1992, J. Exp. Med. 175:377); mite allergen Der p I with human cathepsin and other cysteine proteases (Chua, et al., 1988, J. Exp. Med. 167:175); bee venom allergen phospholipase $A_2$ with human pancreatic enzyme; and bee venom allergen melittin Api m III with human complement C9 (Cf. King et al., 1990, Protein Sequences and Data Analysis 3:263). However, several other major allergens from mite (Chua, et al., 1990, Int. Arch, Allergy Appl. Immunol. 91:124; Tovey, et al., 1989, J. Exp. Med. 170:1457) and ragweed and grass pollens (Rafnar, et al., 1991, J. Biol. Chem. 266:1229; Rogers, et al., 1991, J. Immunol. 147:2547; Silvavovich, et al., 1991, J. Biol. Chem. 266:1204; Singh, et al., 1991, Proc. Natl. Acad. Sci. 88:1384) have no known sequence similarity with other proteins in our environment.

It is a great advantage, therefore, that the gene encoding a vespid phospholipase, Dol m I, has been cloned and sequenced, since recombinant expression of the vespid phospholipase should provide an ample source of protein for testing cross-reactivity and for determination of the relevant B cell and T cell epitopes.

EXAMPLE 2

Yellowjacket Phospholipase

Using the procedures described in Example 1, supra, the cDNA sequence for yellowjacket (*Vespula vulgaris*) phospholipase (Ves v I) was obtained. The complete cDNA sequence and deduced amino acid sequence of Ves v I are shown in FIG. 5 and in SEQ ID NOS: 26 and 27, respectively.

The sequence analysis described in Example 1, supra, was performed on the sequence shown in FIG. 5. Notably, this sequence is identical to that of Dol m I at about ⅔ of the residues. Like Dol m I, Ves v I has about 40% identity in overlaps of 123 residues of mammalian lipases (see FIG. 4). This identity of segments of Ves v I with mammalian lipases is believed to have significance in allergy.

EXAMPLE 3

White Face Hornet Hyaluronidase

Hyaluronidase is one of the three major allergens from white face hornet venom. It is a protein of about 43 kD as estimated by SDS gel electrophoresis (King et al., 1978, Biochem. 17:5165–74). Its enzymatic specificity is of the endo-N-acetylhexosaminidase type (King et al., 1985, Allergy Clin. Immunol. 75:621–628), as it catalyzes the release of reducing groups of N-acetylglucosamine from hyaluronic acid, which is a polymer of repeating disaccharides of D-glucuronic acid and N-acetyl-D-glucosamine.

Partial amino acid sequence data were obtained by Edman degradation of the intact protein and its *S. aureus* protease digested peptides. Two degenerate oligonucleotides, SEQ ID NOS:29 and 31 (Table 2), were synthesized on the basis of partial amino acid sequence data, and they were used as primers in the polymerase chain reaction (PCR) to amplify, from venom cDNAs, the cDNA specific for these primers. The location of oligonucleotide SEQ ID NO:29 in the protein sequence was known and it encodes residue 8–13 of hyaluronidase (SEQ ID NO:28). The location of oligonucleotide SEQ ID NO:31 was established by comparison of the translated sequence of the PCR product with the partial amino acid sequence data of hyaluronidase, and it encodes residue 40–45 (SEQ ID NO:30).

TABLE 2

Oligonucleotide primers for cloning and sequencing of hornet hyaluronidase

| SEQ. ID NO. | Primer | Notes |
|---|---|---|
| 28 | $F^8$  N  I  Y  W  $N^{13}$ | |
| 29 | CGT GGA TCC TCC AAC/T ATI TAC/T TGG AA | PCR for residues 8–45 and sequencing primer. |
| 30 | $D^{45}$G  Q  F  D  $D^{40}$ | |
| 31 | CGT AGA TCT TC ICC T/CTG A/GAA A/GTC A/GTC | See above. |
| 32 | $W^{12}$ N  V  P  T  F  $M^{18}$ | |
| 33 | TGG AAC GTT CCT ACC TTT ATG | First round 3' RACE. |
| 34 | $G^{23}$  L  Y  F  D  $E^{28}$ | |
| 35 | GGC CTA TAC TTC GAC GAG | Second Round 3' RACE and sequencing primer. |
| 36 | $Y^{182}$ G  Y  Y  G  $W^{177}$ | |
| 37 | G ATA TCC GTA ATA GCC CC | cDNA synthesis of 5' RACE. |
| 38 | $D^{107}$ I  V  G  I  $G^{102}$ | |
| 39 | TC  GAT CAC ACC GAT ACC  G | First round 5' RACE. |
| 40 | $L^{62}$ P  L  L  A  $P^{57}$ | |
| 41 | AG CGG CAA CAA TGC CGG G | Second round 5' RACE and sequencing primer. |
| 42 | AAG GTA CCG TCG ACA TCG ATA ATA CGA | cDNA synthesis of 3' |
| 43 | CTC ACT ATA GGG ATT $T_{15}$ | RACE or first round 5' RACE. |
| 44 | AAG GAT CCG TCG ACA TC | First round 3' RACE or second round 5' RACE. |
| 45 | GAC ATC GAT AAT ACG AC | Second round 3' RACE and sequencing primer. |
| 46 | $S^1$  E  R  P  K  $R^6$ | |
| 47 | CGT GGA TCC GAG AGA CCG AAA AGA | PCR for residue 1–331 and sequencing primer. |
| 48 | $N^{331}$ V  T  E  T  $V^{326}$ | |
| 49 | CGT AGA TCT GTT GAC GGT TTC CGT CAC | See above. |
| 50 | $I^{106}$ D  F  E  R  $W^{111}$ | |
| 51 | ATC GAC TTT GAA AGA TGG | Sequencing primer. |

TABLE 2-continued

Oligonucleotide primers for cloning and sequencing of hornet hyaluronidase

| SEQ. ID NO. | Primer | Notes |
|---|---|---|
| 52 | M$^{161}$ E E T L K$^{166}$ | |
| 53 | CGT GGA TCC ATG GAG GAA ACT TTG AA | Sequencing primer. |

From the DNA sequence data encoding residue 8–45 of hyaluronidase, additional oligonucleotide primers, SEQ ID NOS:33 and 35 (Table 2), were synthesized. They were used together with oligonucleotides SEQ ID NOS: 44 and 45 to amplify the 3' ends of the cDNA encoding hyaluronidase by the procedure of Frohman et al. (1988, Proc. Natl. Acad. Sci. USA 85:8998–9002), which is commonly known as Rapid Amplification of cDNA Ends (RACE). In this manner, a cDNA fragment containing nucleotides 127–1229 (FIG. 6; SEQ ID NO:54) was obtained. Another set of primers SEQ ID NOS:37, 39 and 41 (Table 2), were synthesized based on the DNA sequence data of 3' RACE. They were used together with primer SEQ ID NOS: 43 and 44, to amplify the 5' end of the cDNA following the RACE protocol, and the cDNA fragment containing nucleotides 1–246 was obtained.

The N-terminal sequence of hyaluronidase for residue 1–45, which was deduced by Edman degradation, is encoded by nucleotide position 61–204 in FIG. 6 (SEQ ID NO:54). The region of nucleotide position 1–60 probably encodes a portion of the "prepro" segment of hyaluronidase. However, the presence of a stop codon at nucleotide position 19–21 is unexpected, and it may possibly represent incomplete splicing of mRNA. The coding region of the DNA in FIG. 6 ends at position 1053, as a stop codon follows that position. The region of nucleotide position 1057–1229 represents the 3'-untranslated region with a poly A tail but without a polyadenylation signal site of AATAAA.

Oligonucleotide primers SEQ ID NOS:47 and 49 (Table 2) were synthesized from the data in FIG. 6 (SEQ ID NO:54). They were used to amplify the cDNA encoding full length hyaluronidase for expression in bacteria.

DNA fragments from 3' or 5' RACE and PCR for expression of hyaluronidase were cloned into pCR vector (Invitrogen Corp., San Diego, Calif.). Plasmid DNAs were isolated from appropriate clones, then sequenced by Sanger dideoxynucleotide chain-termination method using a Sequenase version 2.0 kit (U.S. Biochemical, Cleveland, Ohio). The DNA sequence in FIG. 6 (SEQ ID NO:54) was assembled from the data of 5 clones from 3' RACE, 4 clones from 5' RACE and one clone from specific PCR for expression of hyaluronidase. There are sufficient overlaps of the sequence data of these clones so that every nucleotide position in FIG. 6 (SEQ ID NO:54) represents the consensus of 4 or more clones. The only exception is the region of position 1–45 which was obtained from 2 clones. There are several mutations of these clones which are listed in Table 3. Most of them are silent mutations but 2 of them result in amino acid substitutions. These mutations may be due to infidelity of base incorporation in PCR, or they may represent allelic forms.

TABLE 3

Sequence mutations of clones from 3' and 5' RACE and expression PCR*

| Source/clone | Nucleotides at indicated positions | | | | | | | | | |
|---|---|---|---|---|---|---|---|---|---|---|
| | 151 | 199 | 251 | 259 | 642 | 1064 | 1137 | 1154 | 1172 | 1184 |
| 5' RACE | | | | | | | | | | |
| #9 | A | | | | | | | | | |
| #19 | A | A | | | | | | | | |
| #32 | A | A | | | | | | | | |
| #39 | G | A | | | | | | | | |
| Expression #12 | A | T | A | T | C | | | | | |
| 3' RACE | | | | | | | | | | |
| #1 | | A | A | G | C | A | T | G | G | A | T |
| #2 | | | A | A | T | A | T | A | A | A | T |
| #3 | | | | | | | T | A | A | G | T |
| #4 | | | A | A | T | A | | | | | |
| #7 | | | | | | | C | A | A | A | A |
| Consensus | A | A | A | T | A | T | A | A | A | T |

*The consensus sequence is given in FIG. 6 (SEQ ID NO:54). A mutation at position 151 results in a codon change from AAT for asparagine to GAT for aspartic acid, and at position 199 from ATC for isoleucine to TTC for phenylalanine. Mutations at positions 251, 259 and 642 did not result in codon changes. The remaining mutations are in the 3' untranslated region.

The deduced amino acid sequence (SEQ ID NO:55) from the DNA data in FIG. 6 (SEQ ID NO:54) indicates hyaluronidase to have 331 amino acid residues with a molecular weight of 38,929 daltons. The molecular weight of hyaluronidase was determined to be about 43 kDa from SDS gel electrophoretic data. The difference in molecular weight most likely indicates that hyaluronidase is a glycoprotein, as the translated sequence has a potential Asn glycosylation motif of Asn•X•Thr/Ser at residue 79–81.

The necessary venom RNAs and all experimental procedures in the above studies are the same as that described in our previous work on hornet antigen 5 and phospholipase (see Example 1, supra, and Fang et al., 1988, Proc. Natl. Acad. Sci. U.S.A. 85:895–899; Lu et al., 1993, J. Immunol. 150:2823–30; Soldatova et al., 1993, FEBS Lettr. 320:145–149).

The similarity of the hornet venom hyaluronidase deduced amino acid sequence to the amino acid sequence of other proteins was evaluated. The sequence search was made at the National Center for Biotechnology Information using the BLAST network service (Altschul et al., 1990, J. Mol. Biol. 215:403–410). The search revealed that hornet venom hyaluronidase (SEQ ID NO:57) has 54% sequence identity with honey bee venom hyaluronidase which contains 351 residues (SEQ ID NO:56) (Omachl and Kreil, 1993, Proc. Natl. Acad. Sci. U.S.A. 90-3569-73). Both venom hyaluronidases show significant sequence homology with a membrane protein of guinea pig sperm (SEQ ID NO:58) (Lathrop et al., 1990, J. Cell Biol. 111:2939–49). These sequence comparisons are shown in FIG. 7. There is 25% sequence identity of hornet and guinea pig proteins. Hybridization studies with genomic libraries showed that this membrane protein, known as PH-20, is widely distributed in mammals including humans. PH-20 believed to play a role in sperm-egg adhesion.

EXAMPLE 4

Antigenic Cross Reactivity of Hornet and Honey Bee Venom Hyaluronidase

Mice of BALB/c strain were immunized biweekly by intraperitoneal route with native hornet or bee venom hyaluronidases in the presence of alum as an adjuvant. Groups of four mice were immunized, at weeks 0, 2, 4 and 6 with 0.2 ml of 10 mg/ml hyaluronidase and 5 mg/ml alum in 0.05 M phosphate buffer, pH 6.2.

Figure 8A:
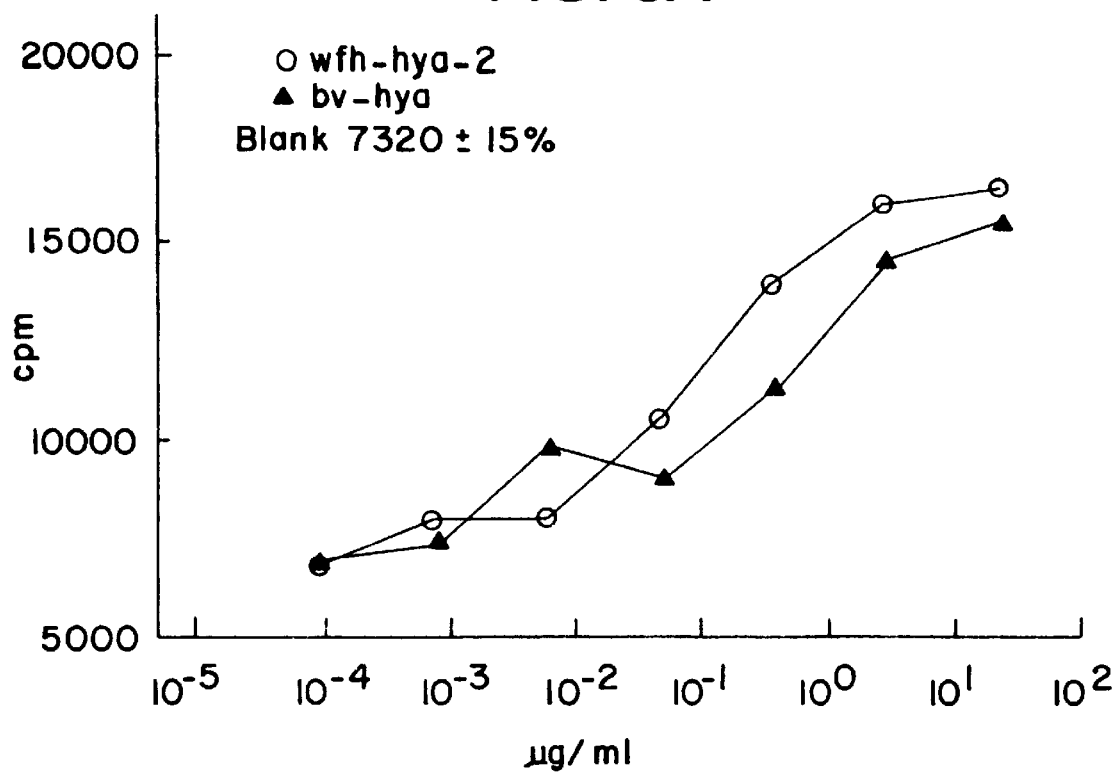
FIG. 8. Proliferation assay with primary spleen cells after two immunizations with hyaluronidase from (A) white-face hornet venom and (B) bee venom. Spleen cells were obtained ten days after two i.p. immunizations with 10 mg/ml venom hyaluronidase in 5 mg/ml alum, spaced two weeks apart. Spleens were removed and leukocytes (4–5× $10^{-6}$ cells/ml) stimulated in vitro with white face hornet venom hyaluronidase (○) or bee venom hyaluronidase (▲) at the indicated concentrations in 96 well culture plates. The final volume of each culture was 200 ml. Proliferation assays were performed in 10R medium supplemental with antibiotics and fetal bovine serum. After three days of incubation, 0.5–1 μCi of $^3$H-thymidine were added to each culture, and the cells harvested 20 hours later. Background $^3$H-Thy incorporations were 7320±9% cpm for (A) and 8500±15% cpm for (B).
Figure 8B:
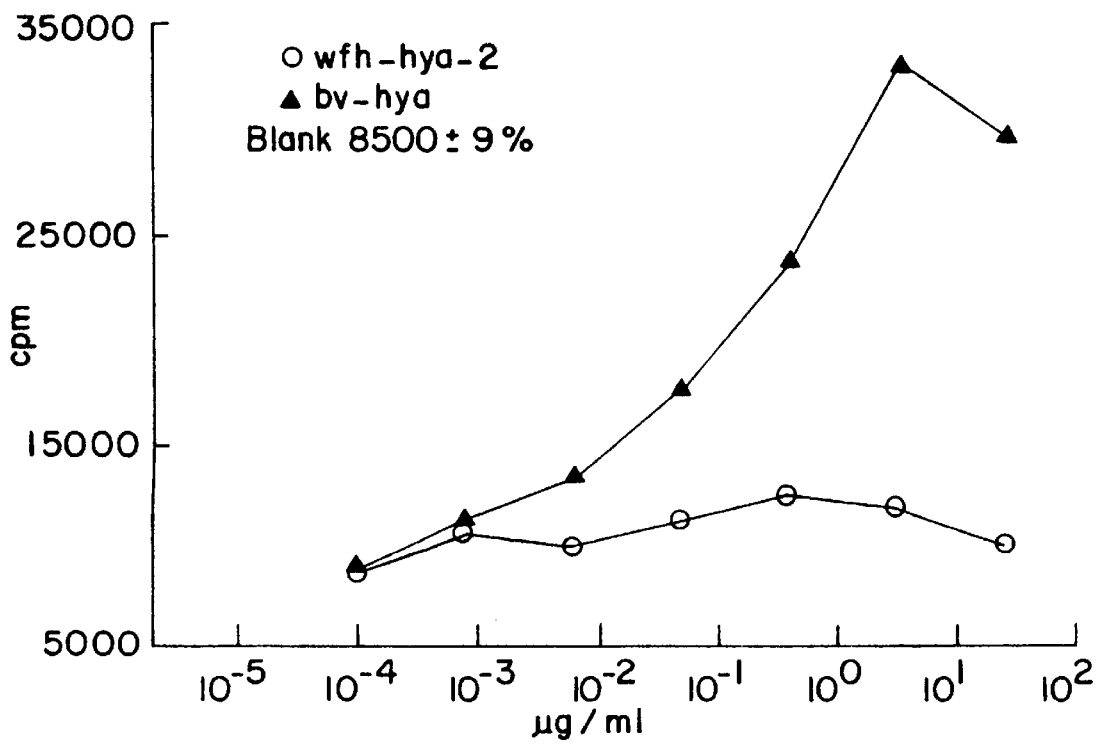

Spleens from immunized mice were obtained for lymphocyte proliferation assays. Proliferation assays at week 3, after two immunizations, showed that spleen cells from mice immunized with hornet hyaluronidase responded equally well on stimulation with hornet or bee protein, and that spleen cells from mice immunized with bee protein responded strongly on stimulation with bee protein but weakly on stimulation with hornet protein (FIGS. 8A and B). Very similar results were obtained when hyaluronidase from yellowjacket (V. vulgaris) or wasp (P. annularis) was used in place of hornet protein as the stimulating antigen in these assays. These findings suggest antigenic cross reaction of the T cell epitopes of bee and vespid hyaluronidases.

Figure 9A:
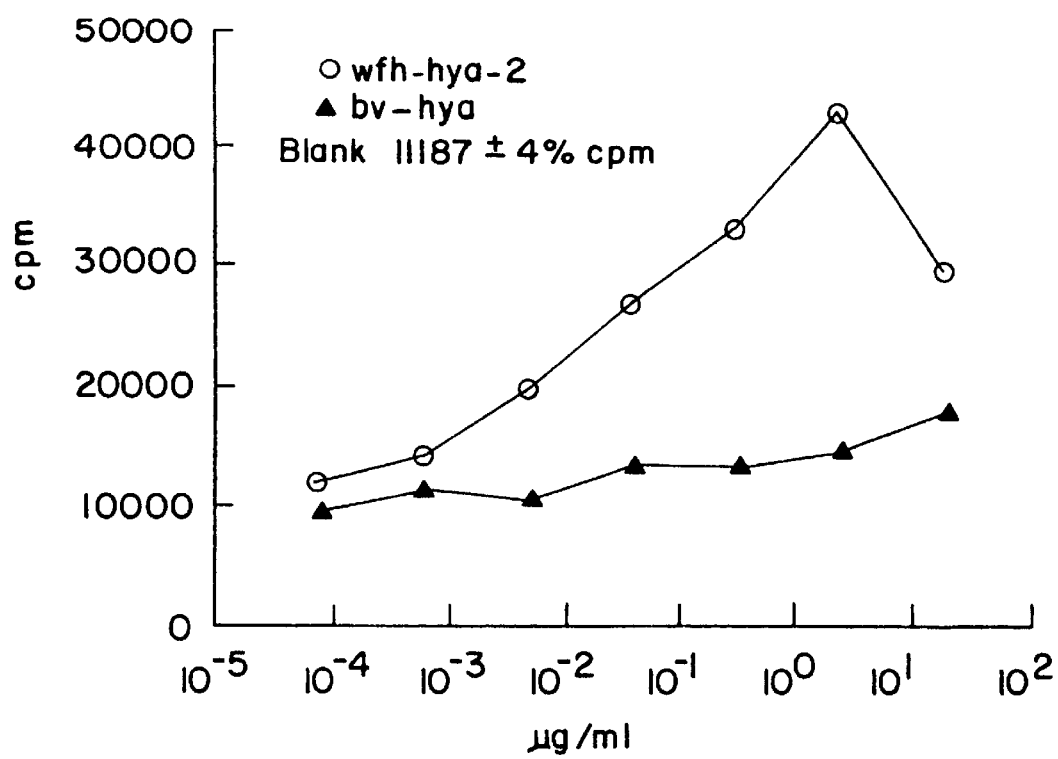
FIG. 9. Proliferation assay with primary spleen cells after five immunizations with (A) white-face hornet venom hyaluronidase and (B) bee venom hyaluronidase. The Figure keys correspond to FIG. 8, and immunizations were performed as described for FIG. 8 spaced two weeks apart. The proliferation assay was also performed as described in FIG. 8. Note that the magnitude of the responses had increased by about 2-fold compared to the mice immunized twice, although the blank values remained about the same. Background $^3$-Thy incorporation was 11187±4% cpm for (A) and 6084±26% cpm for (B).

The long-term responses to immunization were also studied. At week 9, spleen cells from mice immunized with hornet hyaluronidase demonstrated an altered response in vitro, with a significantly greater degree of proliferation in response to hornet hyaluronidase compared to bee hyaluronidase. It appeared that the magnitude of the ,spleen cell response to hornet hyaluronidase increased from week 3 to week 9, whereas the magnitude of the response to bee hyaluronidase remained about the same (FIG. 9A).

Figure 9B:
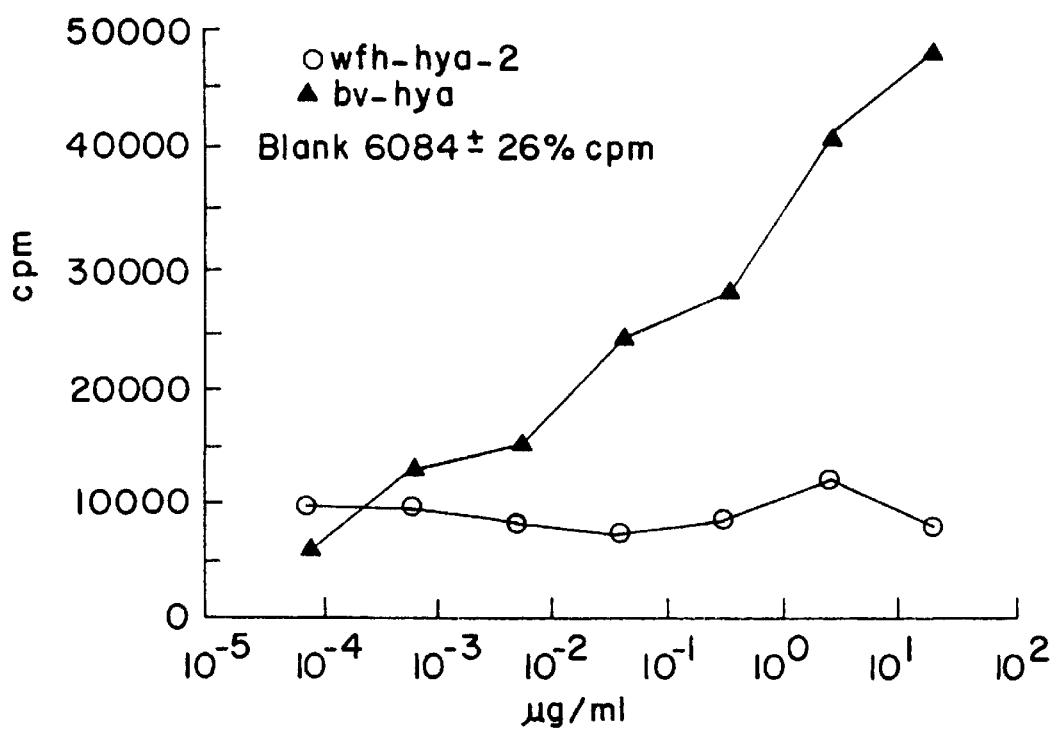

Spleen cells from mice immunized with bee hyaluronidase continued to proliferate in vitro when stimulated with bee hyaluronidase, but responded poorly when stimulated with hornet hyaluronidase (FIG. 9B).

The antibody responses of the mice were also evaluated. Sera were obtained at weeks 0, 5, 7 and assayed for antibodies by ELISA in microtiter wells coated with bee or hornet hyaluronidase. The results of the ELISA are shown in Table 4.

TABLE 4

ANTIBODY TITERS OF BALB/c MICE IMMUNIZED WITH HORNET OR BEE VENOM HYALURONIDASE
Ab TITER

| | BEE HYALURONIDASE-SPECIFIC SERA | | HORNET HYALURONIDASE-SPECIFIC SERA | |
|---|---|---|---|---|
| WEEK | BEE HYA | HORNET HYA | BEE HYA | HORNET HYA |
| 0 | <10 | | | <10 |
| 5 | $1 \times 10^4$ | <10 | 10 | $1 \times 10^4$ |
| 7 | $4 \times 10^4$ | <10 | $2 \times 10^2$ | $5 \times 10^4$ |
| 9 | $3 \times 10^4$ | 10 | $2 \times 10^2$ | $6 \times 10^4$ |

Sera collected at week 7 and 9 showed that hornet venom hyaluronidase-specific antibodies reacted strongly with itself and weekly with the venom hyaluronidase. Bee venom hyaluronidase-specific antibodies reacted only with the immunogen. immunogen.

Knowledge of the antigenic cross reactivity of these two venom proteins is of clinical interest as it is known that there is an association of vespid and bee sensitivity in patients.

EXAMPLE 5

Expression of Functional Hornet Venom Hyaluronidase

Clone 12 in pCR vector of Table 3 contains the cDNA insert encoding residue 1–331 of hornet hyaluronidase. The cDNA insert is flanked by BamHI and BglII restriction sites at its 5' and 3' ends respectively. The insert was excised from the vector by BamHI and BglII digestion, and inserted into cut pQE12 plasmid with complementary cohesive sites (QIAGEN, Chatsworth, Calif.). Mutation at nucleotide position 199 in clone 12 (A→T), resulting in introduction of phenylalanine for isoleucine (see note to Table 3), fortuitously eliminated a BglII site in the coding region of the hyaluronidase.

The recombinant pQE12 plasmid was used to transform competent M15 (pREP) bacteria. On induction of the transformed bacteria with isopropylthiogalactoside, two recombinant proteins of about 43 and 26 kD were expressed. Both proteins were reactive with antibodies specific for hornet hyaluronidase by Western blot. Antibodies used in the Western blot were obtained from the week 9 bleeding of the BALB/c mice as described in Example 4, above.

The pQE12 plasmid is designed so that the recombinant protein has the sequence: MRGS-insert-SRH$_6$. The presence of the hexa-histidine sequence in the recombinant protein makes possible its purification from other bacterial proteins by metal ion chelation chromatography followed by reversed phase chromatography.

The purified recombinant protein was devoid of hyaluronidase activity. Refolding of the recombinant protein in 5 mM 2-mercaptoethanol, 1 mM EDTA, and 2 M guanidine hydrochloride in 0.05 M Tris-HCl buffer of pH 7.4 yielded a product having about 50% of the specific activity of native hyaluronidase. The amount of purified recombinant hyaluronidase was calculated by UV absorbance. Since the purified sample contained both the 23 kD and 46 kD proteins, the actual enzymatic activity of the functional recombinant enzyme may be greater than 50% of that of native hyaluronidase.

The above experiments strongly support the thesis that the 43 kD recombinant protein is the hornet hyaluronidase. The 26 kD recombinant protein may arise due to initiation of translation 3' to the desired site. Such internal states may arise where there is a ribosome binding consensus sequence (Shine-Dalgarno sequence) 5' to an internal ATG or GUG codon.

DEPOSIT OF MICROORGANISMS

A bacterial strain INFαF' containing a recombinant plasmid pCR which has a nucleic acids encoding white face hornet phospholipase, designated WFH-PLA, has been deposited on Mar. 11, 1993 with the American Type Culture Collection (ATCC), 12301 Parklawn Drive, Rockville, Md. 20852, under the provisions of the Budapest Treaty on the International Recognition of the Deposit of Microorganisms for the Purposes of Patent Procedures, and has been assigned ATCC accession number 69254.

The present invention is not to be limited in scope by the microorganisms deposited or the specific embodiments described herein since such embodiments are intended as but single illustrations of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

Various references are cited herein, the disclosures of which are incorporated by reference herein in their entirety.

What is claimed is:

1. An isolated vespid venom hyaluronidase polypeptide having an amino acid sequence as depicted in SEQ ID NO:57, with a modification selected from the group consisting of an aspartic acid for an asparagine at residue number 31 and a phenylalanine for an isoleucine at residue number 47.

2. A vespid venom hyaluronidase fusion protein comprising an immunomodulatory polypeptide fragment of a vespid venom hyaluronidase encoded by a nucleic acid of SEQ ID NO:54.

3. The fusion protein according to claim 2, wherein the fusion protein further comprises a polyhistidine polypeptide.

4. The fusion protein according to claim 2, wherein the vespid venom hyaluronidase is from a vespid of a genus Dolichovespula.

5. The fusion protein according to claim 4, wherein the vespid venom hyaluronidase is from a species maculata.

6. The fusion protein according to claim 5, wherein the vespid venom hyaluronidase has an amino acid sequence as depicted in SEQ ID NO:57.

7. A composition comprising the polypeptide of claim 1 and a pharmaceutically acceptable carrier.

8. A composition comprising the fusion protein of claim 2 and a pharmaceutically acceptable carrier.

9. A method for treating a vespid venom allergen-specific allergic condition comprising administering a therapeutically effective dose of the polypeptide of claim 1 to a subject suffering from the allergic condition.

10. A method for treating a vespid venom allergen-specific allergic condition comprising administering a therapeutically effective dose of the fusion protein of claim 2 to a subject suffering from the allergic condition.

11. A method of preparing a composition comprising mixing the polypeptide of claim 1 with a pharmaceutically acceptable carrier.

12. A method of preparing a composition comprising mixing the fusion protein of claim 2 with a pharmaceutically acceptable carrier.

* * * * *

```
                         SEQUENCE LISTING (1) GENERAL INFORMATION:

(iii) NUMBER OF SEQUENCES: 62

(2) INFORMATION FOR SEQ ID NO: 1:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

AAGGATCCGT CGACATCGAT AATACGACTC ACTATAGGGA TTT                      43

(2) INFORMATION FOR SEQ ID NO: 2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

AAGGATCCGT CGACATC                                                    17

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

GACATCGATA ATACGAC                                                    17
```

(2) INFORMATION FOR SEQ ID NO: 4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Asp Thr Val Lys Met Ile
1               5
```

(2) INFORMATION FOR SEQ ID NO: 5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
GAYACNGTNA ARATGAT                                              17
```

(2) INFORMATION FOR SEQ ID NO: 6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Lys His Asp Phe Tyr Thr
1               5
```

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
AARCAYGAYT TYTAYAC                                              17
```

(2) INFORMATION FOR SEQ ID NO: 8:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Ile Gln Val Tyr His Ala Asp
1               5
```

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

```
ATYTGNACRT ARTGNGCRTC                                          20
```

(2) INFORMATION FOR SEQ ID NO: 10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Pro Tyr Glu Asp Thr Cys
1               5
```

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

```
GGRTAYTCRT CNGTRCA                                             17
```

(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Met Leu Ala Glu Ser
1               5
```

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

```
GCATAAGAGC CTCTGAC                                             17
```

(2) INFORMATION FOR SEQ ID NO: 14:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 14:

```
Met Thr Asp Leu Thr
1               5
```

(2) INFORMATION FOR SEQ ID NO: 15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

```
TCATTGTATC TAGCGTA                                          17
```

(2) INFORMATION FOR SEQ ID NO: 16:

(i) SEQUENCE CHARACTERISTICS:
        (A) LENGTH: 1050 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..951

(xi) SEQUENCE DESCRIPTION: SEQ ID NO: 16:

```
AGA TTA ATA ATG TTC GTA GGT GAT CCG TCG TCA TCA AAT GAA TTA GAT      48
Arg Leu Ile Met Phe Val Gly Asp Pro Ser Ser Ser Asn Glu Leu Asp
 1               5                  10                  15

AGA TTC TCC GTA TGT CCC TTT AGT AAT GAT ACA GTT AAG ATG ATT TTT      96
Arg Phe Ser Val Cys Pro Phe Ser Asn Asp Thr Val Lys Met Ile Phe
                20                  25                  30

TTA ACA AGG GAA AAC CGA AAA CAT GAT TTT TAT ACG CTA GAT ACA ATG     144
Leu Thr Arg Glu Asn Arg Lys His Asp Phe Tyr Thr Leu Asp Thr Met
            35                  40                  45

AAC AGG CAC AAT GAA TTT AAG AAG TCA ATC ATA AAA CGT CCA GTT GTA     192
Asn Arg His Asn Glu Phe Lys Lys Ser Ile Ile Lys Arg Pro Val Val
        50                  55                  60

TTC ATT ACG CAT GGT TTT ACT TCG TCT GCA ACC GAA AAA AAT TTC GTT     240
Phe Ile Thr His Gly Phe Thr Ser Ser Ala Thr Glu Lys Asn Phe Val
 65                  70                  75                  80

GCT ATG TCA GAG GCT CTT ATG CAT ACA GGT GAT TTT CTT ATA ATT ATG     288
Ala Met Ser Glu Ala Leu Met His Thr Gly Asp Phe Leu Ile Ile Met
                85                  90                  95

GTC GAT TGG CGG ATG GCT GCT TGT ACT GAT GAA TAC CCA GGT CTG AAG     336
Val Asp Trp Arg Met Ala Ala Cys Thr Asp Glu Tyr Pro Gly Leu Lys
                100                 105                 110

TAT ATG TTT TAT AAG GCT GCC GTT GGT AAT ACA CGC TTA GTT GGA AAT     384
Tyr Met Phe Tyr Lys Ala Ala Val Gly Asn Thr Arg Leu Val Gly Asn
            115                 120                 125

TTT ATC GCT ATG ATC GCA AAG AAA CTT GTA GAA CAA TAT AAA GTG CCG     432
```

```
Phe Ile Ala Met Ile Ala Lys Lys Leu Val Glu Gln Tyr Lys Val Pro
            130                 135                 140

ATG ACA AAT ATA CGA CTG GTG GGA CAC AGT TTG GGC GCA CAC ATT TCA     480
Met Thr Asn Ile Arg Leu Val Gly His Ser Leu Gly Ala His Ile Ser
145                 150                 155                 160

GGT TTC GCA GGC AAA AGA GTT CAA GAG TTA AAA TTA GGA AAA TTT TCT     528
Gly Phe Ala Gly Lys Arg Val Gln Glu Leu Lys Leu Gly Lys Phe Ser
                165                 170                 175

GAA ATT ATT GGG CTT GAT CCT GCT GGG CCT AGT TTC AAG AAA AAT GAT     576
Glu Ile Ile Gly Leu Asp Pro Ala Gly Pro Ser Phe Lys Lys Asn Asp
            180                 185                 190

TGT TCC GAG AGA ATC TGC GAG ACA GAC GCA CAT TAT GTA CAA ATT TTA     624
Cys Ser Glu Arg Ile Cys Glu Thr Asp Ala His Tyr Val Gln Ile Leu
                195                 200                 205

CAT ACA TCG AGC AAT TTA GGA ACA GAG AGA ACT CTT GGC ACC GTC GAT     672
His Thr Ser Ser Asn Leu Gly Thr Glu Arg Thr Leu Gly Thr Val Asp
210                 215                 220

TTC TAC ATA AAT AAC GGA AGT AAT CAA CCC GGT TGC AGA TAT ATT ATT     720
Phe Tyr Ile Asn Asn Gly Ser Asn Gln Pro Gly Cys Arg Tyr Ile Ile
225                 230                 235                 240

GGA GAA ACT TGC TCT CAT ACG AGA GCC GTG AAA TAC TTT ACC GAG TGC     768
Gly Glu Thr Cys Ser His Thr Arg Ala Val Lys Tyr Phe Thr Glu Cys
                245                 250                 255

ATA AGA CGC GAA TGT TGT TTA ATT GGG GTC CCG CAG TCC AAG AAT CCG     816
Ile Arg Arg Glu Cys Cys Leu Ile Gly Val Pro Gln Ser Lys Asn Pro
            260                 265                 270

CAG CCT GTT TCG AAG TGC ACA AGA AAC GAG TGC GTT TGC GTT GGA TTA     864
Gln Pro Val Ser Lys Cys Thr Arg Asn Glu Cys Val Cys Val Gly Leu
                275                 280                 285

AAC GCA AAG AAA TAT CCT AAA AGG GGC TCA TTT TAT GTA CCG GTT GAA     912
Asn Ala Lys Lys Tyr Pro Lys Arg Gly Ser Phe Tyr Val Pro Val Glu
290                 295                 300

GCT GAA GCT CCA TAT TGC AAT AAC AAC GGG AAA ATA ATT TAATTATATA     961
Ala Glu Ala Pro Tyr Cys Asn Asn Asn Gly Lys Ile Ile
305                 310                 315

AAAAAAACAT TACTATTGAC ACAAGTGCAT TTGTTAATGA TGAAATGAAT AAATTACGAT  1021

TCAAGAAAAA AAAAAAAAAA AAAAAAAA                                    1050

(2) INFORMATION FOR SEQ ID NO: 17:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO: 17:

Arg Leu Ile Met Phe Val Gly Asp Pro Ser Ser Asn Glu Leu Asp
1                 5                  10                  15

Arg Phe Ser Val Cys Pro Phe Ser Asn Asp Thr Val Lys Met Ile Phe
                20                  25                  30

Leu Thr Arg Glu Asn Arg Lys His Asp Phe Tyr Thr Leu Asp Thr Met
            35                  40                  45

Asn Arg His Asn Glu Phe Lys Lys Ser Ile Ile Lys Arg Pro Val Val
        50                  55                  60

Phe Ile Thr His Gly Phe Thr Ser Ser Ala Thr Glu Lys Asn Phe Val
65                  70                  75                  80

Ala Met Ser Glu Ala Leu Met His Thr Gly Asp Phe Leu Ile Ile Met
```

-continued

```
                    85                  90                  95
Val Asp Trp Arg Met Ala Ala Cys Thr Asp Glu Tyr Pro Gly Leu Lys
                100                 105                 110

Tyr Met Phe Tyr Lys Ala Ala Val Gly Asn Thr Arg Leu Val Gly Asn
            115                 120                 125

Phe Ile Ala Met Ile Ala Lys Lys Leu Val Glu Gln Tyr Lys Val Pro
        130                 135                 140

Met Thr Asn Ile Arg Leu Val Gly His Ser Leu Gly Ala His Ile Ser
145                 150                 155                 160

Gly Phe Ala Gly Lys Arg Val Gln Glu Leu Lys Leu Gly Lys Phe Ser
                165                 170                 175

Glu Ile Ile Gly Leu Asp Pro Ala Gly Pro Ser Phe Lys Lys Asn Asp
            180                 185                 190

Cys Ser Glu Arg Ile Cys Glu Thr Asp Ala His Tyr Val Gln Ile Leu
        195                 200                 205

His Thr Ser Ser Asn Leu Gly Thr Glu Arg Thr Leu Gly Thr Val Asp
    210                 215                 220

Phe Tyr Ile Asn Asn Gly Ser Asn Gln Pro Gly Cys Arg Tyr Ile Ile
225                 230                 235                 240

Gly Glu Thr Cys Ser His Thr Arg Ala Val Lys Tyr Phe Thr Glu Cys
                245                 250                 255

Ile Arg Arg Glu Cys Cys Leu Ile Gly Val Pro Gln Ser Lys Asn Pro
            260                 265                 270

Gln Pro Val Ser Lys Cys Thr Arg Asn Glu Cys Val Cys Val Gly Leu
        275                 280                 285

Asn Ala Lys Lys Tyr Pro Lys Arg Gly Ser Phe Tyr Val Pro Val Glu
    290                 295                 300

Ala Glu Ala Pro Tyr Cys Asn Asn Asn Gly Lys Ile Ile
305                 310                 315
```

(2) INFORMATION FOR SEQ ID NO: 18:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

```
Tyr Pro Val Ser Ala Gly Tyr Thr Lys Leu Val Gly Gln Asp Val Ala
1               5                   10                  15

Arg Phe Ile Asn Trp Met Glu Glu Phe Asn Tyr Pro Leu Asp Asn
            20                  25                  30

Val His Leu Leu Gly Tyr Ser Leu Gly Ala His Ala Ala Gly Ile Ala
        35                  40                  45

Gly Ser Leu Thr Asn Lys Lys Val Asn Arg Ile Thr Gly Leu Asp Pro
50                  55                  60

Ala Gly Pro Asn Phe Glu Tyr Ala Glu Ala Pro Ser Arg Leu Ser Pro
65                  70                  75                  80

Asp Asp Ala Asp Phe Val Asp Val Leu His Thr Phe Thr Arg Gly Ser
                85                  90                  95

Pro Gly Arg Ser Ile Gly Ile Gln Lys Pro Val Gly His Val Asp Ile
            100                 105                 110

Tyr Pro Asn Gly Gly Thr Phe Gln Pro Gly Cys
```

115             120

(2) INFORMATION FOR SEQ ID NO: 19:

(i) SEQUENCE CHARACTERISTICS:
       (A) LENGTH: 123 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 19:

Tyr Pro Val Ser Ala Gly Tyr Thr Lys Leu Val Gly Asn Asp Val Ala
1               5                   10                  15

Arg Phe Ile Asn Trp Met Glu Glu Phe Asn Tyr Pro Leu Asp Asn
            20                  25                  30

Val His Leu Leu Gly Tyr Ser Leu Gly Ala His Ala Ala Gly Val Ala
            35                  40                  45

Gly Ser Leu Thr Asn Lys Lys Val Asn Arg Ile Thr Gly Leu Asp Pro
50                  55                  60

Ala Gly Pro Asn Phe Glu Tyr Ala Glu Ala Pro Ser Arg Leu Ser Pro
65                  70                  75                  80

Asp Asp Ala Asp Phe Val Asp Val Leu His Thr Phe Thr Arg Gly Ser
                85                  90                  95

Pro Gly Arg Ser Ile Gly Ile Gln Lys Pro Val Gly His Val Asp Ile
                100                 105                 110

Tyr Pro Asn Gly Gly Thr Phe Gln Pro Gly Cys
            115                 120

(2) INFORMATION FOR SEQ ID NO: 20:

(i) SEQUENCE CHARACTERISTICS:
       (A) LENGTH: 125 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 20:

Tyr Thr Ile Ala Val Arg Asn Thr Arg Leu Val Gly Lys Glu Val Ala
1               5                   10                  15

Ala Leu Leu Arg Trp Leu Glu Glu Ser Val Gln Leu Ser Arg Ser His
            20                  25                  30

Val His Leu Ile Gly Tyr Ser Leu Gly Ala His Val Ser Gly Phe Ala
            35                  40                  45

Gly Ser Ser Ile Gly Gly Thr His Lys Ile Gly Arg Ile Thr Gly Leu
50                  55                  60

Asp Ala Ala Gly Pro Leu Phe Glu Gly Ser Ala Pro Ser Asn Arg Leu
65                  70                  75                  80

Ser Pro Asp Asp Ala Asn Phe Val Asp Ala Ile His Thr Phe Thr Arg
                85                  90                  95

Glu His Met Gly Leu Ser Val Gly Ile Lys Gln Pro Ile Gly His Tyr
                100                 105                 110

Asp Phe Tyr Pro Asn Gly Gly Ser Phe Gln Pro Gly Cys
            115                 120                 125

(2) INFORMATION FOR SEQ ID NO: 21:

```
    (i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Tyr Thr Gln Ala Ser Tyr Asn Thr Arg Val Leu Gly Ala Glu Ile Ala
1               5                  10                  15

Phe Leu Val Gln Val Leu Ser Thr Glu Met Gly Tyr Ser Pro Glu Asn
            20                  25                  30

Val His Leu Ile Pro His Ser Leu Gly Ser His Val Ala Gly Glu Ala
            35                  40                  45

Gly Arg Arg Leu Glu Gly His Val Gly Arg Ile Thr Gly Leu Asp Pro
    50                  55                  60

Ala Glu Pro Cys Phe Gln Gly Leu Pro Glu Val Arg Leu Asp Pro
65                  70                  75                  80

Ser Asp Ala Met Phe Val Asp Val Ile His Thr Asp Ser Ala Pro Ile
                85                  90                  95

Ile Pro Tyr Leu Gly Phe Gly Met Ser Gln Lys Val Gly His Leu Asp
            100                 105                 110

Phe Phe Pro Asn Gly Gly Lys Glu Ile Pro Gly Cys
            115                 120

(2) INFORMATION FOR SEQ ID NO: 22:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Tyr Lys Ala Ala Val Gly Asn Thr Arg Leu Val Gly Asn Phe Ile Ala
1               5                  10                  15

Met Ile Ala Lys Lys Leu Val Glu Gln Tyr Lys Val Pro Met Thr Asn
            20                  25                  30

Ile Arg Leu Val Gly His Ser Leu Gly Ala His Ile Ser Gly Phe Ala
            35                  40                  45

Gly Lys Arg Val Gln Glu Leu Lys Leu Gly Lys Phe Ser Glu Ile Ile
    50                  55                  60

Gly Leu Asp Pro Ala Gly Pro Ser Phe Lys Lys Asn Asp Cys Ser Glu
65                  70                  75                  80

Arg Ile Cys Glu Thr Asp Ala His Tyr Val Gln Ile Leu His Thr Ser
                85                  90                  95

Ser Asn Leu Gly Thr Glu Arg Thr Leu Gly Thr Val Asp Phe Tyr Ile
            100                 105                 110

Asn Asn Gly Ser Asn Gln Pro Gly Cys
            115                 120

(2) INFORMATION FOR SEQ ID NO: 23:

(i) SEQUENCE CHARACTERISTICS:
        (A) LENGTH: 8 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO: 23:

Val Asn Arg His Asn Gln Phe Arg
1               5

(2) INFORMATION FOR SEQ ID NO: 24:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Leu Lys Arg His Asn Asp Phe Arg
1               5

(2) INFORMATION FOR SEQ ID NO: 25:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Met Asn Arg His Asn Glu Phe Lys
1               5

(2) INFORMATION FOR SEQ ID NO: 26:

(i) SEQUENCE CHARACTERISTICS:
        (A) LENGTH: 1341 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 153..1052

(xi) SEQUENCE DESCRIPTION: SEQ ID NO: 26:

```
ATTTCCGGGT AAGTTTGTGT ACGTTTCTAC ACAAAACAAA AATCATGGAA GAAAATATGA        60

ATTTAAAGTA TTTATTATTA TTCGTGTATT TTGTGCAAGT GTTAAATTGT TGCTATGGAC       120

ATGGTGATCC GTTATCTTAC GAATTAGATA GA GGA CCC AAA TGT CCT TTT AAT        173
                                  Gly Pro Lys Cys Pro Phe Asn
                                   1               5

TCT GAT ACA GTT TCG ATA ATT ATT GAA ACA AGG GAA AAC CGA AAT CGT        221
Ser Asp Thr Val Ser Ile Ile Ile Glu Thr Arg Glu Asn Arg Asn Arg
         10                  15                  20

GAT CTT TAT ACA CTA CAG ACA TTA CAG AAT CAT CCT GAA TTT AAG AAA        269
Asp Leu Tyr Thr Leu Gln Thr Leu Gln Asn His Pro Glu Phe Lys Lys
     25                  30                  35

AAA ACT ATA ACA CGT CCA GTT GTA TTC ATT ACA CAT GGT TTT ACT TCA        317
Lys Thr Ile Thr Arg Pro Val Val Phe Ile Thr His Gly Phe Thr Ser
 40                  45                  50                  55

TCT GCA AGT GAA ACA AAT TTC ATA AAT TTA GCA AAA GCT TTG GTA GAT        365
Ser Ala Ser Glu Thr Asn Phe Ile Asn Leu Ala Lys Ala Leu Val Asp
```

-continued

```
                  60                      65                      70
AAA GAT AAC TAT ATG GTT ATC TCA ATC GAT TGG CAG ACG GCT GCT TGT     413
Lys Asp Asn Tyr Met Val Ile Ser Ile Asp Trp Gln Thr Ala Ala Cys
             75                  80                  85

ACT AAT GAA GCT GCA GGT TTA AAG TAT TTA TAT TAT CCT ACT GCT GCT     461
Thr Asn Glu Ala Ala Gly Leu Lys Tyr Leu Tyr Tyr Pro Thr Ala Ala
         90                  95                 100

AGA AAT ACA CGT TTA GTT GGA CAA TAT ATC GCT ACG ATT ACC CAG AAA     509
Arg Asn Thr Arg Leu Val Gly Gln Tyr Ile Ala Thr Ile Thr Gln Lys
        105                 110                 115

CTC GTA AAA CAC TAT AAA ATC TCG ATG GCA AAT ATA CGA TTA ATT GGA     557
Leu Val Lys His Tyr Lys Ile Ser Met Ala Asn Ile Arg Leu Ile Gly
120                 125                 130                 135

CAT AGC TTA GGA GCA CAT GCT TCA GGT TTT GCA GGC AAA AAG GTT CAA     605
His Ser Leu Gly Ala His Ala Ser Gly Phe Ala Gly Lys Lys Val Gln
                140                 145                 150

GAG TTA AAA TTA GGA AAA TAT TCT GAA ATT ATT GGG CTT GAT CCT GCT     653
Glu Leu Lys Leu Gly Lys Tyr Ser Glu Ile Ile Gly Leu Asp Pro Ala
            155                 160                 165

AGG CCT TCG TTC GAT TCA AAT CAT TGT TCC GAA AGA CTC TGC GAG ACA     701
Arg Pro Ser Phe Asp Ser Asn His Cys Ser Glu Arg Leu Cys Glu Thr
        170                 175                 180

GAT GCA GAA TAT GTT CAA ATT ATA CAT ACA TCA AAC TAT TTA GGA ACC     749
Asp Ala Glu Tyr Val Gln Ile Ile His Thr Ser Asn Tyr Leu Gly Thr
185                 190                 195

GAA AAA ACC CTT GGT ACC GTC GAT TTC TAC ATG AAT AAC GGA AAG AAT     797
Glu Lys Thr Leu Gly Thr Val Asp Phe Tyr Met Asn Asn Gly Lys Asn
200                 205                 210                 215

CAA CCT GGT TGC GGT AGA TTT TTC TCA GAA GTT TGC TCT CAT TCG AGA     845
Gln Pro Gly Cys Gly Arg Phe Phe Ser Glu Val Cys Ser His Ser Arg
                220                 225                 230

GCC GTG ATA TAC ATG GCT GAG TGC ATA AAA CAC GAA TGT TGT TTA ATT     893
Ala Val Ile Tyr Met Ala Glu Cys Ile Lys His Glu Cys Cys Leu Ile
            235                 240                 245

GGG ATA CCG AAG TCA AAG AGT TCG CAG CCT ATT TCG TCG TGC ACA AAA     941
Gly Ile Pro Lys Ser Lys Ser Ser Gln Pro Ile Ser Ser Cys Thr Lys
        250                 255                 260

CAG GAG TGC GTT TGC GTT GGA TTA AAC GCA AAG AAG TAT ACT AGT AGA     989
Gln Glu Cys Val Cys Val Gly Leu Asn Ala Lys Lys Tyr Thr Ser Arg
265                 270                 275

GGC TCA TTT TAT GTA CCG GTT GAA AGT ACT GTT CCT TTT TGC AAT AAC    1037
Gly Ser Phe Tyr Val Pro Val Glu Ser Thr Val Pro Phe Cys Asn Asn
280                 285                 290                 295

AAG GGG AAG ATA ATT TAATAATATA AAAAGTAAT TTCCATTCAT CGAAATGCAT     1092
Lys Gly Lys Ile Ile
                300

TTGTTAATGG TGAATGAATA AATTACCATT TAACAAATAA TCGTACATGC AGAATGTCGT  1152

CCAAAATAAT TGCGGAGTAT ATAATGGATG ATCTTAGCAA ATTTAAAAAA TAAAAGAAT   1212

TATATAAACA TATACCCTAT TTGATTTTGC TTTTTAGTTG TAGTGAATTG AATTTTTCTG  1272

TCTGCTTAAT TTGAAACTGC TTCCTTGCTT CTGAATAAAT GCCTGTAAAC ATAAAAAAAA  1332

AAAAAAAA                                                          1341
```

(2) INFORMATION FOR SEQ ID NO: 27:

(i) SEQUENCE CHARACTERISTICS:
        (A) LENGTH: 300 amino acids
        (B) TYPE: amino acid
        (D) TOPOLOGY: linear (ii) MOLECULE TYPE: protein (xi) SEQUENCE DESCRIPTION: SEQ ID NO: 27:

```
Gly Pro Lys Cys Pro Phe Asn Ser Asp Thr Val Ser Ile Ile Ile Glu
 1               5                  10                  15

Thr Arg Glu Asn Arg Asn Arg Asp Leu Tyr Thr Leu Gln Thr Leu Gln
             20                  25                  30

Asn His Pro Glu Phe Lys Lys Lys Thr Ile Thr Arg Pro Val Val Phe
             35                  40                  45

Ile Thr His Gly Phe Thr Ser Ser Ala Ser Glu Thr Asn Phe Ile Asn
         50                  55                  60

Leu Ala Lys Ala Leu Val Asp Lys Asp Asn Tyr Met Val Ile Ser Ile
 65                  70                  75                  80

Asp Trp Gln Thr Ala Ala Cys Thr Asn Glu Ala Ala Gly Leu Lys Tyr
                 85                  90                  95

Leu Tyr Tyr Pro Thr Ala Ala Arg Asn Thr Arg Leu Val Gly Gln Tyr
                100                 105                 110

Ile Ala Thr Ile Thr Gln Lys Leu Val Lys His Tyr Lys Ile Ser Met
            115                 120                 125

Ala Asn Ile Arg Leu Ile Gly His Ser Leu Gly Ala His Ala Ser Gly
        130                 135                 140

Phe Ala Gly Lys Lys Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
                165                 170                 175

Ser Glu Arg Leu Cys Glu Thr Asp Ala Glu Tyr Val Gln Ile Ile His
            180                 185                 190

Thr Ser Asn Tyr Leu Gly Thr Glu Lys Thr Leu Gly Thr Val Asp Phe
        195                 200                 205

Tyr Met Asn Asn Gly Lys Asn Gln Pro Gly Cys Gly Arg Phe Phe Ser
210                 215                 220

Glu Val Cys Ser His Ser Arg Ala Val Ile Tyr Met Ala Glu Cys Ile
225                 230                 235                 240

Lys His Glu Cys Cys Leu Ile Gly Ile Pro Lys Ser Lys Ser Ser Gln
                245                 250                 255

Pro Ile Ser Ser Cys Thr Lys Gln Glu Cys Val Cys Val Gly Leu Asn
            260                 265                 270

Ala Lys Lys Tyr Thr Ser Arg Gly Ser Phe Tyr Val Pro Val Glu Ser
        275                 280                 285

Thr Val Pro Phe Cys Asn Asn Lys Gly Lys Ile Ile
290                 295                 300
```

(2) INFORMATION FOR SEQ ID NO: 28:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal

```
        (xi) SEQUENCE DESCRIPTION: SEQ ID NO: 28:

Phe Asn Ile Tyr Trp Asn
1               5

(2) INFORMATION FOR SEQ ID NO: 29:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 29:

CGTGGATCCT CCAAYATNTA YTGGAA                                          26

(2) INFORMATION FOR SEQ ID NO: 30:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 30:

Asp Gly Gln Phe Asp Asp
1               5

(2) INFORMATION FOR SEQ ID NO: 31:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 31:

CTRCTRAARG TYCCNCTTCT AGATGC                                          26

(2) INFORMATION FOR SEQ ID NO: 32:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO
```

(v) FRAGMENT TYPE: internal (xi) SEQUENCE DESCRIPTION: SEQ ID NO: 32:

Trp Asn Val Pro Thr Phe Met
1               5

(2) INFORMATION FOR SEQ ID NO: 33:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 33:

TGGAACGTTC CTACCTTTAT G                                                  21

(2) INFORMATION FOR SEQ ID NO: 34:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 34:

Gly Leu Tyr Phe Asp Glu
1               5

(2) INFORMATION FOR SEQ ID NO: 35:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 35:

GGCCTATACT TCGACGAG                                                      18

(2) INFORMATION FOR SEQ ID NO: 36:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 36:

Tyr Gly Tyr Tyr Gly Trp
1               5

(2) INFORMATION FOR SEQ ID NO: 37:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 37:

CCCCGATAAT GCCTATAG                                                         18

(2) INFORMATION FOR SEQ ID NO: 38:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 38:

Asp Ile Val Gly Ile Gly
1               5

(2) INFORMATION FOR SEQ ID NO: 39:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 39:

GCCATAGCCA CACTAGCT                                                         18

(2) INFORMATION FOR SEQ ID NO: 40:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 40:

Leu Pro Leu Leu Ala Pro
1               5

(2) INFORMATION FOR SEQ ID NO: 41:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 41:

GGGCCGTAA CAACGGCGA                                                        18

(2) INFORMATION FOR SEQ ID NO: 42:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 42:

AGCATAATAG CTACAGCTGC CTAGGAA                                              27

(2) INFORMATION FOR SEQ ID NO: 43:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 43:

TTTAGGGATA TCACTC                                                          16

(2) INFORMATION FOR SEQ ID NO: 44:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 44:

CTACAGCTGC CTAGGAA                                                        17

(2) INFORMATION FOR SEQ ID NO: 45:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 45:

CAGCATAATA GCTACAG                                                        17

(2) INFORMATION FOR SEQ ID NO: 46:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 46:

Ser Glu Arg Pro Lys Arg
1               5

(2) INFORMATION FOR SEQ ID NO: 47:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 47:

CGTGGATCCG AGAGACCGAA AAGA                                                24

(2) INFORMATION FOR SEQ ID NO: 48:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 48:

Asn Val Thr Glu Thr Val
1               5

(2) INFORMATION FOR SEQ ID NO: 49:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 49:

CACTGCCTTT GGCAGTTGTC TAGATGC                                                 27

(2) INFORMATION FOR SEQ ID NO: 50:

(i) SEQUENCE CHARACTERISTICS:
              (A) LENGTH: 6 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 50:

Ile Asp Phe Glu Arg Trp
1               5

(2) INFORMATION FOR SEQ ID NO: 51:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 51:

ATCGACTTTG AAAGATGG                                                           18

(2) INFORMATION FOR SEQ ID NO: 52:

(i) SEQUENCE CHARACTERISTICS:
              (A) LENGTH: 6 amino acids

```
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 52:

Met Glu Glu Thr Leu Lys
 1               5

(2) INFORMATION FOR SEQ ID NO: 53:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 53:

CGTGGATCCA TGGAGGAAAC TTTGAA                                         26

(2) INFORMATION FOR SEQ ID NO: 54:

(i) SEQUENCE CHARACTERISTICS:
            (A) LENGTH: 1229 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: CDS
            (B) LOCATION: 61..1056

(xi) SEQUENCE DESCRIPTION: SEQ ID NO: 54:

TATATATATC ACCACCGATG ACATCTCCCG CCTAACTTTT CCAGATCGAA TTGCGAAAAA        60

TCC GAG AGA CCG AAA AGA GTC TTC AAC ATT TAT TGG AAC GTT CCT ACC        108
Ser Glu Arg Pro Lys Arg Val Phe Asn Ile Tyr Trp Asn Val Pro Thr
 1               5                  10                  15

TTT ATG TGT CAT CAG TAT GGC CTA TAC TTC GAC GAG GTT ACA AAT TTT        156
Phe Met Cys His Gln Tyr Gly Leu Tyr Phe Asp Glu Val Thr Asn Phe
                20                  25                  30

AAT ATA AAG CAT AAT TCT AAG GAC GAT TTC CAG GGT GAC AAG ATC TCA        204
Asn Ile Lys His Asn Ser Lys Asp Asp Phe Gln Gly Asp Lys Ile Ser
            35                  40                  45

ATT TTT TAT GAT CCT GGA GAA TTC CCG GCA TTG TTG CCG CTC AAA GAA        252
Ile Phe Tyr Asp Pro Gly Glu Phe Pro Ala Leu Leu Pro Leu Lys Glu
        50                  55                  60

GGC AAT TAT AAG ATA AGA AAC GGA GGA GTT CCT CAA GAA GGT AAC ATA        300
Gly Asn Tyr Lys Ile Arg Asn Gly Gly Val Pro Gln Glu Gly Asn Ile
 65                  70                  75                  80
```

```
ACG ATA CAT CTC CAA AGA TTT ATC GAA AAT TTG GAT AAA ACA TAT CCA      348
Thr Ile His Leu Gln Arg Phe Ile Glu Asn Leu Asp Lys Thr Tyr Pro
             85                  90                  95

AAT AGG AAC TTC AAC GGT ATC GGT GTG ATC GAC TTT GAA AGA TGG AGA      396
Asn Arg Asn Phe Asn Gly Ile Gly Val Ile Asp Phe Glu Arg Trp Arg
            100                 105                 110

CCG ATC TTC CGA CAA AAT TGG GGC AAT ATG ATG ATT CAT AAG AAG TTT      444
Pro Ile Phe Arg Gln Asn Trp Gly Asn Met Met Ile His Lys Lys Phe
            115                 120                 125

TCA ATA GAC CTA GTT CGC AAT GAA CAT CCA TTC TGG GAT AAA AAG ATG      492
Ser Ile Asp Leu Val Arg Asn Glu His Pro Phe Trp Asp Lys Lys Met
        130                 135                 140

ATC GAA TTG GAG GCA TCT AAG AGG TTT GAA AAA TAT GCC AGA CTT TTC      540
Ile Glu Leu Glu Ala Ser Lys Arg Phe Glu Lys Tyr Ala Arg Leu Phe
145                 150                 155                 160

ATG GAG GAA ACT TTG AAA TTG GCC AAA AAG ACT AGG AAG CAG GCC GAT      588
Met Glu Glu Thr Leu Lys Leu Ala Lys Lys Thr Arg Lys Gln Ala Asp
                165                 170                 175

TGG GGC TAT TAC GGA TAT CCC TAC TGT TTT AAT ATG TCG CCT AAT AAT      636
Trp Gly Tyr Tyr Gly Tyr Pro Tyr Cys Phe Asn Met Ser Pro Asn Asn
            180                 185                 190

CTC GTA CCC GAT TGT GAC GCT ACA GCG ATG CTC GAG AAC GAC AAG ATG      684
Leu Val Pro Asp Cys Asp Ala Thr Ala Met Leu Glu Asn Asp Lys Met
            195                 200                 205

TCG TGG CTG TTC AAT AAT CAA AAT GTA CTT CTA CCA TCC GTC TAT ATT      732
Ser Trp Leu Phe Asn Asn Gln Asn Val Leu Leu Pro Ser Val Tyr Ile
210                 215                 220

AGA CAC GAA CTG ACC CCT GAT CAA AGA GTT GGT TTA GTC CAA GGA AGA      780
Arg His Glu Leu Thr Pro Asp Gln Arg Val Gly Leu Val Gln Gly Arg
225                 230                 235                 240

GTG AAG GAA GCT GTT AGG ATA TCG AAT AAT TTA AAA CAT TCA CCG AAA      828
Val Lys Glu Ala Val Arg Ile Ser Asn Asn Leu Lys His Ser Pro Lys
                245                 250                 255

GTG CTC TCT TAT TGG TGG TAC GTG TAT CAG GAC GAT ACA AAC ACT TTT      876
Val Leu Ser Tyr Trp Trp Tyr Val Tyr Gln Asp Asp Thr Asn Thr Phe
            260                 265                 270

CTT ACC GAG ACC GAC GTG AAA AAG ACT TTC CAA GAG ATA GCG ATT AAC      924
Leu Thr Glu Thr Asp Val Lys Lys Thr Phe Gln Glu Ile Ala Ile Asn
            275                 280                 285

GGT GGG GAT GGT ATC ATT ATA TGG GGT AGC TCG TCC GAC GTA AAC AGC      972
Gly Gly Asp Gly Ile Ile Ile Trp Gly Ser Ser Ser Asp Val Asn Ser
290                 295                 300

TTA AGT AAA TGT AAG AGA TTA CGG GAG TAT CTG TTG ACG GTT TTG GGA     1020
Leu Ser Lys Cys Lys Arg Leu Arg Glu Tyr Leu Leu Thr Val Leu Gly
305                 310                 315                 320

CCA ATC ACG GTT AAC GTG ACG GAA ACC GTC AAC TAAAGATTAT CCCTAAACTT   1073
Pro Ile Thr Val Asn Val Thr Glu Thr Val Asn
                325                 330

TTAGTACAAT CTATGTAACC TCTTGCCGAT GGCGATAGGT GTGTTCAATG ATCTGCTTTG   1133

CGAACGCTAT CGATGCTGCA ACGATGAATA CTGCGACAAT GCCATCACAT TGAAAAGACT   1193

TTTCGCAGGA AGGAAAAAAA AAAAAAAAAA AAAAA                              1229

(2) INFORMATION FOR SEQ ID NO: 55:

(i) SEQUENCE CHARACTERISTICS:
        (A) LENGTH: 331 amino acids
        (B) TYPE: amino acid
        (D) TOPOLOGY: linear (ii) MOLECULE TYPE: protein
```

(xi) SEQUENCE DESCRIPTION: SEQ ID NO: 55:

Ser Glu Arg Pro Lys Arg Val Phe Asn Ile Tyr Trp Asn Val Pro Thr
1               5                   10                  15

Phe Met Cys His Gln Tyr Gly Leu Tyr Phe Asp Glu Val Thr Asn Phe
            20                  25                  30

Asn Ile Lys His Asn Ser Lys Asp Asp Phe Gln Gly Asp Lys Ile Ser
        35                  40                  45

Ile Phe Tyr Asp Pro Gly Glu Phe Pro Ala Leu Leu Pro Leu Lys Glu
    50                  55                  60

Gly Asn Tyr Lys Ile Arg Asn Gly Gly Val Pro Gln Glu Gly Asn Ile
65                  70                  75                  80

Thr Ile His Leu Gln Arg Phe Ile Glu Asn Leu Asp Lys Thr Tyr Pro
                85                  90                  95

Asn Arg Asn Phe Asn Gly Ile Gly Val Ile Asp Phe Glu Arg Trp Arg
                100                 105                 110

Pro Ile Phe Arg Gln Asn Trp Gly Asn Met Met Ile His Lys Lys Phe
            115                 120                 125

Ser Ile Asp Leu Val Arg Asn Glu His Pro Phe Trp Asp Lys Lys Met
130                 135                 140

Ile Glu Leu Glu Ala Ser Lys Arg Phe Glu Lys Tyr Ala Arg Leu Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Asp Cys Asp Ala Thr Ala Met Leu Glu Asn Asp Lys Met
            195                 200                 205

Ser Trp Leu Phe Asn Asn Gln Asn Val Leu Pro Ser Val Tyr Ile
            210                 215                 220

Arg His Glu Leu Thr Pro Asp Gln Arg Val Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Asp Thr Asn Thr Phe
            260                 265                 270

Leu Thr Glu Thr Asp Val Lys Lys Thr Phe Gln Glu Ile Ala Ile Asn
            275                 280                 285

Gly Gly Asp Gly Ile Ile Ile Trp Gly Ser Ser Ser Asp Val Asn Ser
290                 295                 300

Leu Ser Lys Cys Lys Arg Leu Arg Glu Tyr Leu Leu Thr Val Leu Gly
305                 310                 315                 320

Pro Ile Thr Val Asn Val Thr Glu Thr Val Asn
                325                 330

(2) INFORMATION FOR SEQ ID NO: 56:

(i) SEQUENCE CHARACTERISTICS:
        (A) LENGTH: 343 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 56:

```
Pro Asp Asn Asn Lys Thr Val Arg Glu Phe Asn Val Tyr Trp Asn Val
1               5                   10                  15

Pro Thr Phe Met Cys His Lys Tyr Gly Leu Arg Phe Glu Glu Val Ser
            20                  25                  30

Glu Lys Tyr Gly Ile Leu Gln Asn Trp Met Asp Lys Phe Arg Gly Glu
            35                  40                  45

Glu Ile Ala Ile Leu Tyr Asp Pro Gly Met Phe Pro Ala Leu Leu Lys
    50                  55                  60

Asp Pro Asn Gly Asn Val Val Ala Arg Asn Gly Gly Val Pro Gln Leu
65              70                  75                      80

Gly Asn Leu Thr Lys His Leu Gln Val Phe Arg Asp His Leu Ile Asn
                85                  90                  95

Gln Ile Pro Asp Lys Ser Phe Pro Gly Val Gly Val Ile Asp Phe Glu
            100                 105                 110

Ser Trp Arg Pro Ile Phe Arg Gln Asn Trp Ala Ser Leu Gln Pro Tyr
            115                 120                 125

Lys Lys Leu Ser Val Glu Val Val Arg Arg Glu His Pro Phe Trp Asp
130                 135                 140

Asp Gln Arg Val Glu Gln Glu Ala Lys Arg Arg Phe Glu Lys Tyr Gly
145                 150                 155                 160

Gln Leu Phe Met Glu Glu Thr Leu Lys Ala Ala Lys Arg Met Arg Pro
                165                 170                 175

Ala Ala Asn Trp Gly Tyr Tyr Ala Tyr Pro Tyr Cys Tyr Asn Leu Thr
                180                 185                 190

Pro Asn Gln Pro Ser Ala Gln Cys Glu Ala Thr Thr Met Gln Glu Asn
                195                 200                 205

Asp Lys Met Ser Trp Leu Phe Glu Ser Glu Asp Val Leu Leu Pro Ser
            210                 215                 220

Val Tyr Leu Arg Trp Asn Leu Thr Ser Gly Glu Arg Val Gly Leu Val
225                 230                 235                 240

Gly Gly Arg Val Lys Glu Ala Leu Arg Ile Ala Arg Gln Met Thr Thr
                245                 250                 255

Ser Arg Lys Lys Val Leu Pro Tyr Tyr Trp Tyr Lys Tyr Gln Asp Arg
                260                 265                 270

Arg Asp Thr Asp Leu Ser Arg Ala Asp Leu Glu Ala Thr Leu Arg Lys
            275                 280                 285

Ile Thr Asp Leu Gly Ala Asp Gly Phe Ile Ile Trp Gly Ser Ser Asp
            290                 295                 300

Asp Ile Asn Thr Lys Ala Lys Cys Leu Gln Phe Arg Glu Tyr Leu Asn
305                 310                 315                 320

Asn Glu Leu Gly Pro Ala Val Lys Arg Ile Ala Leu Asn Asn Asn Ala
                325                 330                 335

Asn Asp Arg Leu Thr Val Asp
                340
```

(2) INFORMATION FOR SEQ ID NO: 57:

(i) SEQUENCE CHARACTERISTICS:
        (A) LENGTH: 331 amino acids
        (B) TYPE: amino acid
        (C) STRANDEDNESS: single
        (D) TOPOLOGY: linear -continued (ii) MOLECULE TYPE: peptide (iii) HYPOTHETICAL: NO (iv) ANTI-SENSE: NO (xi) SEQUENCE DESCRIPTION: SEQ ID NO: 57:

```
Ser Glu Arg Pro Lys Arg Val Phe Asn Ile Tyr Trp Asn Val Pro Thr
1               5                   10                  15

Phe Met Cys His Gln Tyr Gly Leu Tyr Phe Asp Glu Val Thr Asn Phe
                20                  25                  30

Asn Ile Lys His Asn Ser Lys Asp Asp Phe Gln Gly Asp Lys Ile Ser
                35                  40                  45

Ile Phe Tyr Asp Pro Gly Glu Phe Pro Ala Leu Leu Pro Leu Lys Glu
50                      55                  60

Gly Asn Tyr Lys Ile Arg Asn Gly Gly Val Pro Gln Glu Gly Asn Ile
65                      70                  75                  80

Thr Ile His Leu Gln Arg Phe Ile Glu Asn Leu Asp Lys Thr Tyr Pro
                85                  90                  95

Asn Arg Asn Phe Asn Gly Ile Gly Val Ile Asp Phe Glu Arg Trp Arg
                100                 105                 110

Pro Ile Phe Arg Gln Asn Trp Gly Asn Met Met Ile His Lys Lys Phe
                115                 120                 125

Ser Ile Asp Leu Val Arg Asn Glu His Pro Phe Trp Asp Lys Lys Met
130                     135                 140

Ile Glu Leu Glu Ala Ser Lys Arg Phe Glu Lys Tyr Ala Arg Leu Phe
145                     150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
                180                 185                 190

Leu Val Pro Asp Cys Asp Ala Thr Ala Met Leu Glu Asn Asp Lys Met
                195                 200                 205

Ser Trp Leu Phe Asn Asn Gln Asn Val Leu Leu Pro Ser Val Tyr Ile
                210                 215                 220

Arg His Glu Leu Thr Pro Asp Gln Arg Val Gly Leu Val Gln Gly Arg
225                     230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Asp Thr Asn Thr Phe
                260                 265                 270

Leu Thr Glu Thr Asp Val Lys Lys Thr Phe Gln Glu Ile Ala Ile Asn
                275                 280                 285

Gly Gly Asp Gly Ile Ile Ile Trp Gly Ser Ser Ser Asp Val Asn Ser
290                     295                 300

Leu Ser Lys Cys Lys Arg Leu Arg Glu Tyr Leu Leu Thr Val Leu Gly
305                     310                 315                 320

Pro Ile Thr Val Asn Val Thr Glu Thr Val Asn
                325                 330
```

(2) INFORMATION FOR SEQ ID NO: 58:

(i) SEQUENCE CHARACTERISTICS:
        (A) LENGTH: 344 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 58:

```
Ala Pro Pro Leu Ile Pro Asn Val Pro Leu Leu Trp Val Trp Asn Ala
1               5                   10                  15

Pro Thr Glu Pro Cys Ile Gly Gly Thr Asn Gln Pro Leu Asp Met Ser
            20                  25                  30

Phe Phe Ser Ile Val Gly Thr Pro Arg Lys Asn Ile Thr Gly Gln Ser
            35                  40                  45

Ile Thr Leu Tyr Tyr Val Asp Arg Leu Gly Tyr Tyr Pro Tyr Ile Asp
    50                  55                  60

Pro His Thr Gly Ala Ile Val His Gly Gly Leu Pro Gln Leu Met Asn
65                  70                  75                  80

Leu Gln Gln His Leu Arg Lys Ser Arg Gln Asp Ile Leu Phe Tyr Met
                85                  90                  95

Pro Thr Asp Ser Val Gly Leu Ala Val Ile Asp Trp Glu Glu Trp Arg
            100                 105                 110

Pro Thr Trp Tyr Arg Asn Trp Arg Pro Lys Asp Ile Tyr Arg Asn Lys
            115                 120                 125

Ser Ile Glu Leu Val Lys Ser Gln His Pro Gln Tyr Asn His Ser Tyr
    130                 135                 140

Ala Val Ala Val Ala Lys Arg Asp Phe Glu Arg Thr Gly Lys Ala Phe
145                 150                 155                 160

Met Leu Glu Thr Leu Lys Leu Gly Lys Ser Leu Arg Pro Ser Ser Leu
                165                 170                 175

Trp Gly Tyr Tyr Leu Phe Pro Asp Cys Tyr Asn Thr His Phe Thr Lys
            180                 185                 190

Pro Asn Tyr Asp Gly His Cys Pro Pro Ile Glu Leu Gln Arg Asn Asn
            195                 200                 205

Asp Leu Gln Trp Leu Trp Asn Asp Ser Thr Ala Leu Tyr Pro Ser Val
    210                 215                 220

Tyr Leu Thr Ser Arg Val Arg Ser Ser Gln Asn Gly Ala Leu Tyr Val
225                 230                 235                 240

Arg Asn Arg Val His Glu Ser Ile Arg Val Ser Lys Leu Met Asp Asp
                245                 250                 255

Lys Asn Pro Leu Pro Ile Tyr Val Tyr Ile Arg Leu Val Phe Thr Asp
            260                 265                 270

Gln Thr Thr Thr Phe Leu Glu Leu Asp Asp Leu Val His Ser Val Gly
            275                 280                 285

Glu Ile Val Pro Leu Gly Val Ser Gly Ile Ile Ile Trp Gly Ser Leu
            290                 295                 300

Ser Leu Thr Arg Ser Leu Val Ser Cys Ile Gly Leu Glu Asn Tyr Met
305                 310                 315                 320

Lys Gly Thr Leu Leu Pro Tyr Leu Ile Asn Val Thr Leu Ala Ala Lys
                325                 330                 335

Met Cys Gly Gln Val Leu Cys Lys
            340
```

(2) INFORMATION FOR SEQ ID NO: 59:

(i) SEQUENCE CHARACTERISTICS:

```
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 59:

Phe Ser Val Cys Pro Phe
1               5

(2) INFORMATION FOR SEQ ID NO: 60:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 60:

CGTGGATCCT TCTCCGTATG TCCCTTT                                              27

(2) INFORMATION FOR SEQ ID NO: 61:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 61:

Ile Ile Lys Gly Asn Asn
1               5

(2) INFORMATION FOR SEQ ID NO: 62:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 62:

CGTAGATCTA ATTATTTTCC CGTTGTT                                              27
```